US012807351B2

(12) United States Patent
Goodly et al.

(10) Patent No.: US 12,807,351 B2
(45) Date of Patent: Nov. 24, 2026

(54) PACKAGED FEMININE HYGIENE PAD PRODUCT ADAPTED FOR DISCREET CARRY AND ACCESS, AND MANUFACTURING PROCESS

(71) Applicant: The Procter & Gamble Company, Cincinnati, OH (US)

(72) Inventors: Benjamin Goodly, Cincinnati, OH (US); Mariangela Caputi, Frankfurt am Main (DE); Caroline Carriel Schmitt, Alemanha (DE); Andrew Saksa, Cincinnati, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 0 days.

(21) Appl. No.: 18/950,283

(22) Filed: Nov. 18, 2024

(65) Prior Publication Data

US 2026/0138767 A1 May 21, 2026

(51) Int. Cl.

*B65B 25/14* (2006.01)
*A61F 13/551* (2006.01)
*B65B 51/02* (2006.01)

(52) U.S. Cl.

CPC ........ *B65B 25/145* (2013.01); *A61F 13/5514* (2013.01); *B65B 51/02* (2013.01)

(58) Field of Classification Search

CPC ....... B65B 25/145; B65B 51/02; B65B 5/045; A61F 13/5514; A61F 13/5513;

(Continued)

(56) References Cited

U.S. PATENT DOCUMENTS 3,078,201 A 2/1963 Christie
3,381,441 A 5/1968 Condo, Jr. et al.

(Continued)

FOREIGN PATENT DOCUMENTS

| | | | |
|---|---|---|---|
| CA | 2785189 | A1 | 7/2011 |
| CN | 1074110 | A | 7/1993 |
| CN | 1087511 | A | 6/1994 |
| CN | 1163096 | A | 10/1997 |
| CN | 1168292 | A | 12/1997 |
| CN | 1177359 | A | 3/1998 |
| CN | 1368870 | A | 9/2002 |
| CN | 1439348 | A | 9/2003 |
| CN | 1625377 | A | 6/2005 |
| CN | 1875900 | A | 12/2006 |

(Continued)

OTHER PUBLICATIONS

All Office Actions: U.S. Appl. No. 18/950,289, filed Nov. 18, 2024.

(Continued)

*Primary Examiner* — Shelley M Self
*Assistant Examiner* — David G Shutty
(74) *Attorney, Agent, or Firm* — Sarah M. DeCristofaro

(57) ABSTRACT

A process for producing flow-wrapped packaged articles is disclosed. It includes providing a continuous series of successive articles; providing a continuous supply of package film; applying a process adhesive to one or both of the articles and an inward surface of the film; disposing the articles in contact with the inward surface and thereby adhering the articles thereto, conveying the film and the articles to flow wrapping equipment, thereby wrapping the film about the articles and creating a series of flow-wrapped articles; conveying the flow-wrapped articles to seaming equipment to form seams between successive leading and trailing articles, thereby forming a series of individually enveloping structures about individual articles; and conveying the series of individually enveloping structures to cutting, separating and/or perforating equipment, to form separate or separable individual packaged articles.

17 Claims, 16 Drawing Sheets

(58) Field of Classification Search
CPC .............. A61F 13/551; A61F 13/15674; A61F 13/15682; A61F 13/15747; A61F 13/15756; A61F 13/55135; B65H 45/1015
See application file for complete search history.

(56) References Cited

U.S. PATENT DOCUMENTS

| | | | | |
|---|---|---|---|---|
| 3,619,336 | A | 11/1971 | Hughes | |
| 3,775,203 | A | 11/1973 | Johnson | |
| 3,929,135 | A | 12/1975 | Thompson | |
| 4,048,003 | A | 9/1977 | Bolli | |
| 4,405,310 | A | 9/1983 | Karami | |
| 4,506,488 | A | 3/1985 | Matt et al. | |
| 4,525,977 | A | 7/1985 | Matt | |
| 4,648,513 | A | 3/1987 | Newman | |
| 4,692,162 | A | 9/1987 | Binker et al. | |
| 4,722,168 | A | 2/1988 | Heaney | |
| 5,242,726 | A | 9/1993 | Pariseau | |
| 5,295,988 | A | 3/1994 | Muckenfuhs et al. | |
| 5,300,054 | A | 4/1994 | Feist | |
| 5,358,499 | A | 10/1994 | Seidy | |
| 5,546,732 | A | 8/1996 | Coleman et al. | |
| 5,799,465 | A | 9/1998 | Townsend | |
| 5,873,869 | A | 2/1999 | Hammons et al. | |
| 5,993,430 | A | 11/1999 | Gossens et al. | |
| 6,234,229 | B1 | 5/2001 | Tabuchi | |
| 6,293,932 | B1 * | 9/2001 | Balzar | A61F 13/5514 604/385.03 |
| 6,302,872 | B1 | 10/2001 | Teranishi et al. | |
| 6,316,688 | B1 | 11/2001 | Hammons | |
| 6,601,706 | B2 | 8/2003 | Mcmanus et al. | |
| 6,896,668 | B2 * | 5/2005 | Kashiwagi | A61F 13/47245 604/385.01 |
| 7,334,682 | B2 | 2/2008 | Goepfert | |
| 7,398,870 | B2 | 7/2008 | Mccabe | |
| 7,908,824 | B2 * | 3/2011 | Kuroda | A61F 13/5514 53/135.2 |
| 8,460,260 | B2 * | 6/2013 | Fung | A61F 13/5514 206/436 |
| 8,545,470 | B2 * | 10/2013 | Fung | A61F 13/5514 604/385.03 |
| 8,568,378 | B2 * | 10/2013 | Fung | A61F 13/5514 604/385.03 |
| 9,011,399 | B2 * | 4/2015 | Fung | B65B 69/00 604/385.02 |
| 9,011,400 | B2 * | 4/2015 | Fung | A61F 13/5514 604/385.02 |
| 9,186,284 | B1 | 11/2015 | Hernandez | |
| 9,211,219 | B2 * | 12/2015 | Fung | B65B 5/045 |
| 9,610,202 | B2 * | 4/2017 | Rezai | A61L 15/58 |
| 10,932,962 | B2 | 3/2021 | Drewnowski et al. | |
| 11,234,871 | B2 | 2/2022 | Kuramochi | |
| 11,712,379 | B2 * | 8/2023 | Agami | A61F 13/472 604/385.02 |
| 11,878,438 | B1 | 1/2024 | Boesel et al. | |
| 12,029,634 | B2 * | 7/2024 | Agami | A61F 13/15674 |
| 12,037,154 | B2 | 7/2024 | Lester et al. | |
| 2001/0056270 | A1 * | 12/2001 | Mizutani | A61F 13/551 604/385.02 |
| 2002/0084203 | A1 | 7/2002 | Cottingham et al. | |
| 2002/0125105 | A1 | 9/2002 | Nakakado | |
| 2002/0132106 | A1 | 9/2002 | Dyer et al. | |
| 2002/0183709 | A1 | 12/2002 | Munsch | |
| 2003/0073962 | A1 | 4/2003 | Olsen et al. | |
| 2004/0173492 | A1 | 9/2004 | Kane et al. | |
| 2004/0186450 | A1 * | 9/2004 | Hermansson | B65D 75/58 604/385.01 |
| 2005/0115665 | A1 | 6/2005 | Saraf | |
| 2005/0131371 | A1 | 6/2005 | Fell | |
| 2005/0137553 | A1 | 6/2005 | Bechyne et al. | |
| 2005/0148979 | A1 | 7/2005 | Palma et al. | |
| 2005/0154365 | A1 | 7/2005 | Zander et al. | |
| 2005/0227410 | A1 | 10/2005 | Colella et al. | |
| 2005/0261651 | A1 | 11/2005 | Lima et al. | |
| 2006/0025739 | A1 | 2/2006 | Dipalma | |
| 2006/0185797 | A1 | 8/2006 | Lauzon et al. | |
| 2007/0233031 | A1 | 10/2007 | Benson | |
| 2009/0105680 | A1 * | 4/2009 | Amiot | A61F 13/5514 604/385.13 |
| 2009/0105681 | A1 * | 4/2009 | Chicoine | A61F 13/5514 604/385.01 |
| 2010/0108268 | A1 | 5/2010 | Yamamoto et al. | |
| 2010/0262090 | A1 | 10/2010 | Riesinger | |
| 2010/0263336 | A1 | 10/2010 | Uttaro et al. | |
| 2010/0307114 | A1 | 12/2010 | Spiekers et al. | |
| 2011/0028931 | A1 | 2/2011 | Fung | |
| 2013/0190711 | A1 | 7/2013 | Hashino et al. | |
| 2013/0291486 | A1 | 11/2013 | Shinomori et al. | |
| 2015/0119837 | A1 | 4/2015 | Thompson, Jr. et al. | |
| 2015/0313763 | A1 | 11/2015 | Bagger-sjbck | |
| 2015/0374560 | A1 | 12/2015 | Hubbard, Jr. | |
| 2016/0089279 | A1 | 3/2016 | Barbosa et al. | |
| 2016/0235592 | A1 | 8/2016 | Coe et al. | |
| 2016/0287452 | A1 | 10/2016 | Hubbard, Jr. | |
| 2017/0112678 | A1 | 4/2017 | Pelland | |
| 2017/0151105 | A1 | 6/2017 | Holmberg | |
| 2018/0353354 | A1 * | 12/2018 | Lee | A61F 13/5511 |
| 2019/0177021 | A1 | 6/2019 | Tulchinski et al. | |
| 2019/0254890 | A1 | 8/2019 | Yonaha | |
| 2019/0291900 | A1 | 9/2019 | Persson et al. | |
| 2019/0366646 | A1 | 12/2019 | Peregi et al. | |
| 2020/0229985 | A1 | 7/2020 | Agami et al. | |
| 2020/0229990 | A1 | 7/2020 | Agami et al. | |
| 2020/0229991 | A1 | 7/2020 | Agami et al. | |
| 2021/0330856 | A1 * | 10/2021 | Caputi | C09J 153/02 |
| 2023/0135421 | A1 * | 5/2023 | Toro | A61F 13/47 604/365 |
| 2023/0310231 | A1 | 10/2023 | Agami et al. | |
| 2024/0315890 | A1 | 9/2024 | Maldonado | |
| 2024/0315891 | A1 | 9/2024 | Agami et al. | |

FOREIGN PATENT DOCUMENTS

| | | | | | |
|---|---|---|---|---|---|
| CN | 101600407 | A | | 12/2009 | |
| CN | 102470053 | A | | 5/2012 | |
| CN | 102665629 | A | | 9/2012 | |
| CN | 102753126 | A | | 10/2012 | |
| CN | 103356343 | A | | 10/2013 | |
| CN | 104640576 | A | | 5/2015 | |
| CN | 104869965 | A | | 8/2015 | |
| CN | 106456412 | A | | 2/2017 | |
| CN | 107249537 | A | | 10/2017 | |
| CN | 107530211 | A | | 1/2018 | |
| CN | 108135762 | A | | 6/2018 | |
| CN | 108882995 | A | | 11/2018 | |
| EP | 3378791 | A2 | | 9/2018 | |
| GB | 2059337 | A | | 4/1981 | |
| GB | 2298627 | A | * | 9/1996 | B65D 65/02 |
| GB | 2300402 | A | * | 11/1996 | A61F 13/5514 |
| GB | 2277914 | B | | 6/1997 | |
| JP | 2004298288 | A | | 10/2004 | |
| JP | 2005176869 | A | | 7/2005 | |
| JP | 2018535743 | A | | 12/2018 | |
| WO | 9414396 | A1 | | 7/1994 | |
| WO | 03039424 | A1 | | 5/2003 | |
| WO | 2004069684 | A1 | | 8/2004 | |
| WO | 2007041212 | A1 | | 4/2007 | |
| WO | 2007086034 | A1 | | 8/2007 | |
| WO | 2009136826 | A1 | | 11/2009 | |
| WO | 2013080757 | A1 | | 6/2013 | |

OTHER PUBLICATIONS

All Office Actions: U.S. Appl. No. 18/329,848, filed Jun. 6, 2023.
All Office Actions; U.S. Appl. No. 16/750,074, filed Jan. 23, 2020.
All Office Actions; U.S. Appl. No. 16/750,082, filed Jan. 23, 2020.
All Office Actions; U.S. Appl. No. 16/750,089, filed Jan. 23, 2020.
All Office Actions; U.S. Appl. No. 16/750,095, filed Jan. 23, 2020.
All Office Actions; U.S. Appl. No. 18/731,831, filed Jun. 3, 2024.
Unpublished U.S. Appl. No. 18/950,289, filed Nov. 18, 2024, to Benjamin Goodly et al.

(56) References Cited

OTHER PUBLICATIONS

PCT Search Report and Written Opinion for PCT/US2025/053873 dated Jan. 26, 2026, 11 pages.

* cited by examiner

PACKAGED FEMININE HYGIENE PAD PRODUCT ADAPTED FOR DISCREET CARRY AND ACCESS, AND MANUFACTURING PROCESS

BACKGROUND

Users/consumers of feminine hygiene pads have developed a number of varying expectations and preferences for such products over the years, as the products themselves have evolved. These expectations and preferences include (in no particular order) (1) that the pad have suitable absorption performance such that it will readily accept, absorb, contain, isolate and effectively retain all menstrual fluid discharged, away from the user's skin and without leaking, over a normal time of use/wear; (2) that the pad be as thin (non-bulky), flexible and pliable as possible for purposes of comfort, accommodation of the wearer's body movements, and discreetness of wear under clothing; and (3) that the pad and its packaging provide for convenient and discreet carry, and discreet and easy package opening and access to the pad at the time it is needed (particularly when the user is away from home). Many women may have anxiety about leaving the home during menstruation, and about being sufficiently prepared, while away from home, to effectively address needs relating to absorption and containment of discharged menstrual fluid. In addition to desiring a sufficiently absorbent pad that can be effectively used/worn discreetly under clothing, many women desire discreetness and convenience with respect to having to carry pads with them outside the home, and with respect to having to open and access a packaged pad for use, in situations in which they need to use a bathroom or restroom in an unfamiliar, non-private or otherwise uncomfortable place and/or circumstances.

With respect to currently known product designs and the materials currently known and used as components of these products, these expectations and preferences cannot all be fully satisfied simultaneously. The manufacturer must carefully balance its priorities, to provide product features that address each of these expectations and preferences to greater and lesser extents under competitive cost/pricing constraints, in order to provide a product that will sufficiently please its user/consumer market. For example, absorbent materials that desirably provide absorption capacity also undesirably contribute to bulk when packaged and when worn under clothing, and may also limit flexibility of the pad. Accordingly, when designing its products for maximized consumer satisfaction, the manufacturer must make choices concerning how to prioritize design features and materials selections that affect these characteristics, to strike a balance that will hopefully maximize satisfaction of its consumer market.

Some types of products, which may include feminine hygiene products as contemplated herein, are desirably packaged individually in film packages, wherein the film packages are efficiently created using flow-wrapping and seaming equipment.

In some examples, such as individually-packaged feminine hygiene pads, it may be desired that the size of the packages be minimized. This may be desired because consumers of these products value compactness for convenience of carry and discreetness, and also may be desired for purposes of maximizing efficiency in use of packaging film stock. Minimizing individual package size and maximizing efficient use of film stock require that the package have minimal interior clearance, between the packaged product and the film enclosure.

Due to the relatively pliable and lightweight nature of such products, however, if individual product placement relative the film stock is not carefully controlled and maintained, as the product and film stock are conveyed into and through flow wrapping, seaming, and cutting equipment, individual product may be susceptible to being dislodged from its intended location relative the film, and portions of the product may be unintentionally trapped between jaws or dies of film seaming and/or cutting equipment used to form packages about the product, resulting in defectively packaged and/or damaged product. Consequently, opportunity for reduction or elimination of this problem exists.

Consequently, there is always room for any improvements that can more satisfactorily and simultaneously address consumer preferences for convenience and discreetness of package carry, opening and access, combined with absorption performance, as well as in improved manufacturing processes and product configurations designed for improved efficiency and improved consistency and quality.

DESCRIPTION OF EXAMPLES

Definitions

With respect to a feminine hygiene pad that is open and laid out flat on a horizontal planar surface, "lateral" refers to a direction perpendicular to the longitudinal direction and parallel the horizontal planar surface. "Width" refers to a dimension measured along a lateral direction.

With respect to a feminine hygiene pad that is open and laid out flat on a horizontal planar surface and having a length measured from its forwardmost end to its rearwardmost end, "longitudinal" refers to a direction parallel with the line along which the length is measured, and parallel to the horizontal planar surface. "Length" refers to a dimension measured in the longitudinal direction.

With respect to a feminine hygiene pad, the terms "front," "rear," "forward" and "rearward" relate to features or regions of the pad in a position as it would ordinarily be worn by a user, and the front and rear of the user's body when standing.

With respect to a feminine hygiene pad that is open and laid out flat on a horizontal planar surface, "z-direction" refers to a direction perpendicular to the horizontal planar surface. When the pad is being worn by a user (and thus in a curved configuration), "z-direction" at any particular point location on the pad refers to a direction normal to the wearer-facing surface of the pad at the particular point location.

With respect to a feminine hygiene pad, "wearer-facing" is a relative locational term referring to a feature of a component or structure of the pad that when in use that lies closer to the wearer than another feature of the component or structure that lies along the same z-direction. For example, a topsheet has a wearer-facing surface that lies closer to the wearer than the opposite, outward-facing surface of the topsheet.

With respect to a feminine hygiene pad, "outward-facing" is a relative locational term referring to a feature of a component or structure of the pad that when in use that lies farther from the wearer than another feature of the component or structure that lies along the same z-direction. For example, a topsheet has an outward-facing surface that lies farther from the wearer than the opposite, wearer-facing surface of the topsheet.

DESCRIPTION

Figure 1:
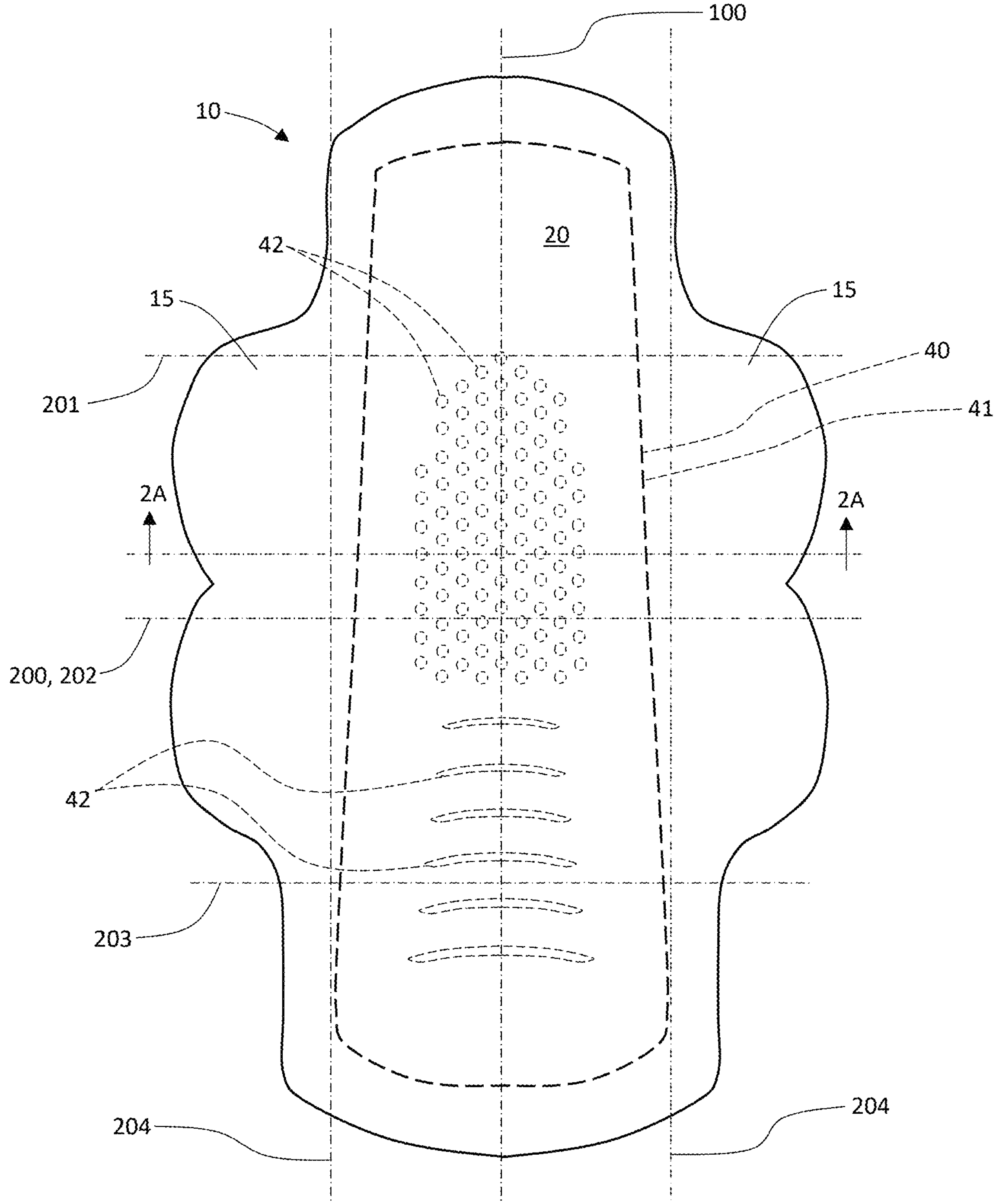
FIG. 1 is a plan view of a feminine hygiene pad, open and laid out flat, topsheet side facing the viewer.
Figure 2A:
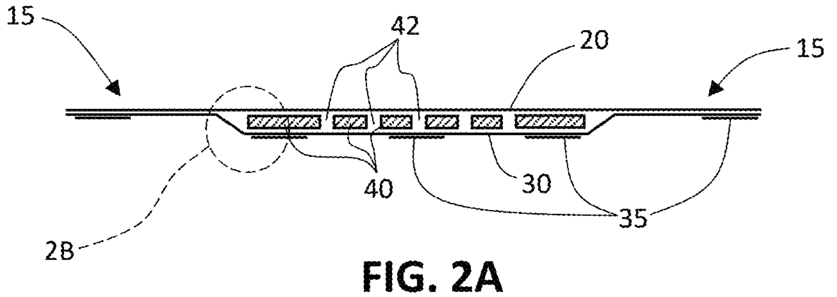
FIG. 2A is a schematic lateral cross section of the feminine hygiene pad of FIG. 1, taken along line 2A-2A in FIG. 1.

Referring to FIGS. 1 and 2A, a feminine hygiene pad 10 may include a liquid permeable topsheet 20, a liquid impermeable backsheet 30 and an absorbent layer 40 disposed between the topsheet and the backsheet. The absorbent layer has an outer perimeter 41. In peripheral regions outside the outer perimeter 41, the topsheet and the backsheet may be bonded together in laminated fashion by any suitable mechanism including but not limited to adhesive bonding, thermal bonding, pressure bonding, etc., thereby retaining and holding the absorbent layer 40 in place between the topsheet 20 and the backsheet 30. Pad 10 may include opposing wing portions 15 extending laterally outside of perimeter 41 by a comparatively greater width dimension than the main portion of the pad. Wing portions 15 may be formed of lateral extensions of the material forming the topsheet 20, backsheet 30, or both together. The outward-facing surface of the backsheet forming the undersides of the main portion and the wing portions may have deposits of panty-fastening adhesive ("PFA") 35 thereon. PFA deposits 35 may be provided to enable the user to adhere the pad to the inside of her underpants in the crotch region thereof, and wrap the wing portions through and around the inside edges of the leg openings of the underpants and adhere them to the outside/underside of the underpants in the crotch region, providing supplemental holding support and helping guard the leg edges of the underpants against soiling. When pad 10 is packaged, PFA deposits 35 may be covered by one or more removable sheets of release film or paper (not shown) that cover the PFA deposits 35 and shield them from contact with other surfaces until the user is ready to remove the sheets and place the pad for use.

To ensure that the pad facilitates sufficiently compact folding and packaging as described herein, it may be desired to limit the length LP of the pad to no greater than 32 cm, more preferably no greater than 29 cm, and even more preferably no greater than 26 cm. Alternatively, or in addition, it may be desired to limit the length LAL of the absorbent layer (also measured in the longitudinal direction) to no greater than 30 cm, more preferably no greater than 27 cm, and even more preferably no greater than 24 cm.

Topsheet

Topsheet 20 may be formed of any suitable liquid permeable web material. Referring back to the figures, the topsheet 20 is positioned adjacent a wearer-facing surface of the absorbent layer 40 and may be joined thereto and to the backsheet 30 by any suitable attachment or bonding method. The topsheet 20 and the backsheet 30 may be joined directly to each other in the peripheral regions outside the perimeter 41 of the absorbent layer 40 and may be indirectly joined by directly joining them respectively to wearer-facing and outward-facing surfaces of the absorbent layer or additional optional layers included with the pad.

Topsheet 20 may be formed of any liquid pervious web material that is suitably compliant, soft feeling, and non-irritating to the wearer's skin. Suitable topsheet materials include a liquid pervious material that contacts the body of the wearer and permits menstrual fluid discharges to rapidly penetrate through it.

A suitable topsheet can be made of various materials such as woven and nonwoven materials; apertured film materials including apertured formed thermoplastic films, apertured plastic films, and fiber-entangled apertured films; hydro-formed thermoplastic films; porous foams; reticulated foams; reticulated thermoplastic films; thermoplastic scrims; or combinations thereof. Some suitable examples of films that can be utilized as topsheets are described in U.S. Pat. Nos. 3,929,135; 4,324,246; 4,342,314; 4,463,045; 5,006,394; 4,609,518; and 4,629,643.

Nonlimiting examples of woven and nonwoven web materials that may be suitable for use as the topsheet include fibrous materials made from natural fibers, modified natural fibers, synthetic fibers, or combinations thereof. Some suitable examples are described in U.S. Pat. Nos. 4,950,264, 4,988,344; 4,988,345; 3,978,185; 7,785,690; 7,838,099; 5,792,404; and 5,665,452.

In some examples, the topsheet may comprise tufts as described in U.S. Pat. Nos. 8,728,049; 7,553,532; 7,172,801; 8,440,286; 7,648,752; and 7,410,683. The topsheet may have a pattern of discrete hair-like fibrils as described in U.S. Pat. No. 7,655,176 or U.S. Pat. No. 7,402,723. Additional examples of suitable topsheet materials include those described in U.S. Pat. Nos. 8,614,365; 8,704,036; 6,025,535 and US 2015/041640. Another suitable topsheet may be formed from a three-dimensional substrate as detailed in US 2017/0258647. The topsheet may have one or more layers, as described in US 2016/0167334; US 2016/0166443; and US 2017/0258651. The topsheet may be apertured, as described in U.S. Pat. No. 5,628,097.

As contemplated herein, component nonwoven web material from which topsheet 20 be cut may be a nonwoven web material that includes or consists predominately (by weight) or entirely of cellulosic plant fibers such as fibers of cotton, flax, hemp, jute or mixtures thereof, that are either naturally hydrophilic or suitably processed so as be rendered hydrophilic (or have increased hydrophilicity) and processed to be suitably soft. Plant-based fibers may be preferred to appeal to consumer preferences for natural products. In other examples, semisynthetic fibers derived from cellulosic material, such as rayon (including viscose, lyocell, MODAL (a product of Lenzing AG, Lenzing, Austria) and cuprammonium rayon) may be used. In some examples a topsheet cut from a carded nonwoven including or consisting predominately (by weight) or entirely of cotton fibers may be preferred. In some examples, the nonwoven web material may be formed via a carding process. In some other examples the nonwoven web material may be formed in a co-forming process in which plant-based fibers of finite lengths are physically blended or mixed with streams of filaments of indefinite lengths, spun from polymeric resin, and laid down on a forming belt to form a web as described in, for example, U.S. Pat. Nos. 8,017,534; 4,100,324; US 2003/0200991; U.S. Pat. No. 5,508,102; US 2003/0211802; EP 0 333 228; WO 2009/10938; US 2017/0000695; US 2017/0002486; U.S. Pat. No. 9,944,047; 2017/0022643 and US 2018/0002848.

For purposes of limiting bulk and caliper (thickness) of the pad for the purpose of providing a thin pad facilitating compact folding and packaging as described below, it may be desired that the topsheet be disposed in direct face-to-face relationship with the absorbent layer, with no intervening layer disposed therebetween. Alternatively, an intervening layer, if included (such as a secondary topsheet or acquisition layer), may be formed of a nonwoven web material having a basis weight no greater than 30 gsm, more preferably no greater than 25 gsm, even more preferably no greater than 20 gsm, and still more preferably no greater than 15 gsm.

Absorbent Layer

Figure 2B:
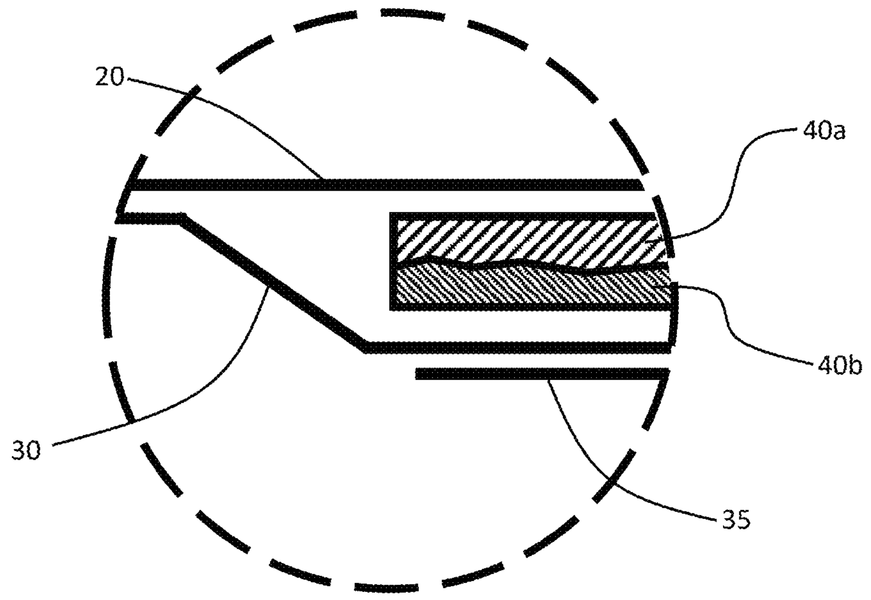
FIG. 2B is a view of portion 2B of the drawing of FIG. 2A, enlarged to depict sublayers of an absorbent layer.
Figure 3:
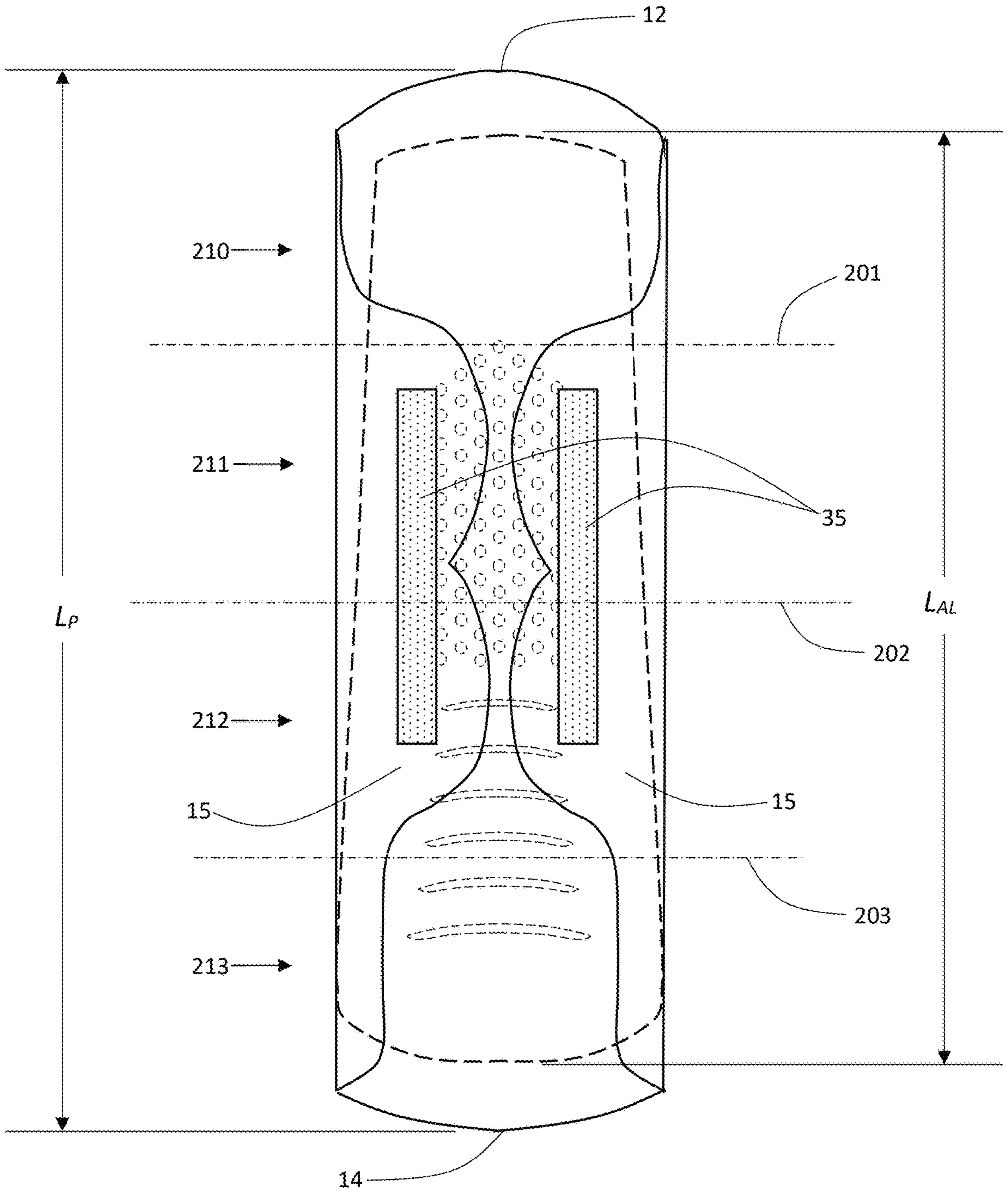
FIG. 3 is a plan view of the feminine hygiene pad of FIG. 1, shown with side portions folded laterally over and inwardly alongside longitudinal fold lines.

In some examples the absorbent layer 40 may be formed of or include a layer of absorbent open-celled foam material. In some examples, the foam material may include at least first and second sublayers 40*a*, 40*b* (FIG. 2B) of absorbent open-celled foam material, the sublayers being in direct face-to-face contact with each other. In such examples, the wearer-facing sublayer may be a relatively larger-celled foam material, and the outward-facing sublayer may be a relatively smaller-celled foam material, for purposes explained in more detail below. In some examples it may be desired that the layer of absorbent open-celled foam material provide the majority, substantially most or all of the absorption capacity of the pad. This feature minimizes the number of components present to impart bulk to the pad when folded and packaged, and when in use.

The open-celled foam material may be a foam material that is manufactured via polymerization of the continuous oil phase of a water-in-oil high internal phase emulsion ("HIPE").

A water-in-oil HIPE has two phases. One phase is a continuous oil phase comprising monomers to be polymerized, and an emulsifier to help stabilize the HIPE. The oil phase may also include one or more photoinitiators. The monomer component may be present in an amount of from about 80% to about 99%, and in certain examples from about 85% to about 95% by weight of the oil phase. The emulsifier component, which is soluble in the oil phase and suitable for forming a stable water-in-oil emulsion may be present in the oil phase in an amount of from about 1% to about 20% by weight of the oil phase. The emulsion may be formed at an emulsification temperature of from about 20° C. to about 130° C. and in certain examples from about 50° C. to about 100° C.

In general, the monomers will include from about 20% to about 97% by weight of the oil phase at least one substantially water-insoluble monofunctional alkyl acrylate or alkyl methacrylate. For example, monomers of this type may include C4-C18 alkyl acrylates and C2-C18 methacrylates, such as ethylhexyl acrylate, butyl acrylate, hexyl acrylate, octyl acrylate, nonyl acrylate, decyl acrylate, isodecyl acrylate, tetradecyl acrylate, benzyl acrylate, nonyl phenyl acrylate, hexyl methacrylate, 2-ethylhexyl methacrylate, octyl methacrylate, nonyl methacrylate, decyl methacrylate, isodecyl methacrylate, dodecyl methacrylate, tetradecyl methacrylate, and octadecyl methacrylate.

The oil phase may also comprise from about 2% to about 40%, and in certain examples from about 10% to about 30%, by weight of the oil phase, a substantially water-insoluble, polyfunctional crosslinking alkyl acrylate or methacrylate. This crosslinking comonomer, or crosslinker, is added to confer strength and resilience to the resulting HIPE foam. Examples of crosslinking monomers of this type comprise monomers containing two or more activated acrylate, methacrylate groups, or combinations thereof. Nonlimiting examples of this group include 1,6-hexanedioldiacrylate, 1,4-butanedioldimethacrylate, trimethylolpropane triacrylate, trimethylolpropane trimethacrylate, 1,1 2-dodecyldimethacrylate, 1,14-tetradecanedioldimethacrylate, ethylene glycol dimethacrylate, neopentyl glycol diacrylate (2,2-dimethylpropanediol diacrylate), hexanediol acrylate methacrylate, glucose pentaacrylate, sorbitan pentaacrylate, and the like. Other examples of crosslinkers contain a mixture of acrylate and methacrylate moieties, such as ethylene glycol acrylate-methacrylate and neopentyl glycol acrylate-methacrylate. The ratio of methacrylate:acrylate group in the mixed crosslinker may be varied from 50:50 to any other ratio as needed.

Any third substantially water-insoluble comonomer may be added to the oil phase in weight percentages of from about 0% to about 15% by weight of the oil phase, in certain examples from about 2% to about 8%, to modify properties of the HIPE foams. In certain cases, "toughening" monomers may be desired which impart toughness to the resulting HIPE foam. These include monomers such as styrene, vinyl chloride, vinylidene chloride, isoprene, and chloroprene. Without being bound by theory, it is believed that such monomers aid in stabilizing the HIPE during polymerization (also known as "curing") to provide a more homogeneous and better formed HIPE foam which results in better toughness, tensile strength, abrasion resistance, and the like. Monomers may also be added to confer flame retardancy as disclosed in U.S. Pat. No. 6,160,028. Monomers may be added to confer color, for example vinyl ferrocene, fluorescent properties, radiation resistance, opacity to radiation, for example lead tetraacrylate, to disperse charge, to reflect incident infrared light, to absorb radio waves, to form a wettable surface on the HIPE foam struts, or for any other desired property in a HIPE foam. In some cases, these additional monomers may slow the overall process of conversion of HIPE to HIPE foam, the tradeoff being necessary if the desired property is to be conferred. Thus, such monomers can be used to slow down the polymerization rate of a HIPE. Examples of monomers of this type comprise styrene and vinyl chloride.

The oil phase may further contain an emulsifier used for stabilizing the HIPE. Emulsifiers used in a HIPE can include: (a) sorbitan monoesters of branched C16-C24 fatty acids; linear unsaturated C16-C22 fatty acids; and linear saturated C12-C14 fatty acids, such as sorbitan monooleate, sorbitan monomyristate, and sorbitan monoesters, sorbitan monolaurate diglycerol monooleate (DGMO), polyglycerol monoisostearate (PGMIS), and polyglycerol monomyristate (PGMM); (b) polyglycerol monoesters of branched C16-C24 fatty acids, linear unsaturated C16-C22 fatty acids, or linear saturated C12-C14 fatty acids, such as diglycerol monooleate (for example diglycerol monoesters of C18:1 fatty acids), diglycerol monomyristate, diglycerol monoisostearate, and diglycerol monoesters; (c) diglycerol monoaliphatic ethers of -branched C16-C24 alcohols, linear unsaturated C16-C22 alcohols, and linear saturated C12-C14 alcohols, and mixtures of these emulsifiers. See U.S. Pat. Nos. 5,287,207 and 5,500,451. Another emulsifier that may be used is polyglycerol succinate (PGS), which is formed from an alkyl succinate, glycerol, and triglycerol.

Such emulsifiers, and combinations thereof, may be added to the oil phase so that they comprise between about 1% and about 20%, in certain examples from about 2% to about 15%, and in certain other examples from about 3% to about 12% by weight of the oil phase In certain examples, coemulsifiers may also be used to provide additional control of cell size, cell size distribution, and emulsion stability, particularly at higher temperatures, for example greater than about 65° C. Examples of coemulsifiers include phosphatidyl cholines and phosphatidyl choline-containing compositions, aliphatic betaines, long chain C12-C22 dialiphatic quaternary ammonium salts, short chain C1-C4 dialiphatic quaternary ammonium salts, long chain C12-C22 dialkoyl(alkenoyl)-2-hydroxyethyl, short chain C1-C4 dialiphatic quaternary ammonium salts, long chain C12-C22 dialiphatic imidazolinium quaternary ammonium salts, short chain C1-C4 dialiphatic imidazolinium quaternary ammonium salts, long chain C12-C22 monoaliphatic benzyl quaternary ammonium salts, long chain C12-C22 dialkoyl(alkenoyl)-2-aminoethyl, short chain C1-C4 monoaliphatic benzyl quaternary ammonium salts, short chain C1-C4 monohydroxyaliphatic quaternary ammonium salts. In certain examples, ditallow dimethyl ammonium methyl sulfate (DTDMAMS) may be used as a coemulsifier.

Photoinitiators may comprise between about 0.05% and about 10%, and in certain examples between about 0.2% and about 10% by weight of the oil phase. Lower amounts of photoinitiator allow light to better penetrate the HIPE foam, which can provide for polymerization deeper into the HIPE foam. However, if polymerization is done in an oxygen-containing environment, there should be enough photoinitiator to initiate the polymerization and overcome oxygen inhibition. Photoinitiators can respond rapidly and efficiently to a light source with the production of radicals, cations, and other species that are capable of initiating a polymerization reaction. The photoinitiators used in forming foams within contemplation of the present disclosure may absorb UV light at wavelengths of about 200 nanometers (nm) to about 800 nm, in certain examples about 250 nm to about 450 nm. If the photoinitiator is in the oil phase, suitable types of oil-soluble photoinitiators include benzyl ketals, α-hydroxyalkyl phenones, α-amino alkyl phenones, and acylphospine oxides. Examples of photoinitiators include 2,4,6-[trimethylbenzoyldiphosphine]oxide in combination with 2-hydroxy-2-methyl-1-phenylpropan-1-one (50:50 blend of the two is sold by Ciba Specialty Chemicals, Ludwigshafen, Germany as DAROCUR 4265); benzyl dimethyl ketal (sold by Ciba Geigy as IRGACURE 651); α-,α-dimethoxy-α-hydroxy acetophenone (sold by Ciba Specialty Chemicals as DAROCUR 1173); 2-methyl-1-[4-(methyl thio)phenyl]-2-morpholino-propan-1-one (sold by Ciba Specialty Chemicals as IRGACURE 907); 1-hydroxycyclohexyl-phenyl ketone (sold by Ciba Specialty Chemicals as IRGACURE 184); bis(2,4,6-trimethylbenzoyl)-phenylphosphineoxide (sold by Ciba Specialty Chemicals as IRGACURE 819); diethoxyacetophenone, and 4-(2-hydroxyethoxy)phenyl-(2-hydroxy-2-methylpropyl) ketone (sold by Ciba Specialty Chemicals as IRGACURE 2959); and Oligo [2-hydroxy-2-methyl-1-[4-(1-methylvinyl)phenyl]propanone] (sold by Lamberti spa, Gallarate, Italy as ESACURE KIP EM).

The dispersed aqueous phase of a HIPE comprises water, and may also comprise one or more components, such as initiator, photoinitiator, or electrolyte, wherein in certain examples, the one or more components are at least partially water soluble.

One component of the aqueous phase may be a water-soluble electrolyte. The water phase may contain from about 0.2% to about 40%, in certain examples from about 2% to about 20%, by weight of the aqueous phase of a water-soluble electrolyte. The electrolyte minimizes the tendency of monomers, comonomers, and crosslinkers that are primarily oil soluble to also dissolve in the aqueous phase. Examples of electrolytes include chlorides or sulfates of alkaline earth metals such as calcium or magnesium and chlorides or sulfates of alkali earth metals such as sodium. Such electrolyte can include a buffering agent for the control of pH during the polymerization, including such inorganic counterions as phosphate, borate, and carbonate, and mixtures thereof. Water soluble monomers may also be used in the aqueous phase, examples being acrylic acid and vinyl acetate.

Another component that may be present in the aqueous phase is a water-soluble free-radical initiator. The initiator can be present at up to about 20 mole percent based on the total moles of polymerizable monomers present in the oil phase. In certain examples, the initiator is present in an amount of from about 0.001 to about 10 mole percent based on the total moles of polymerizable monomers in the oil phase. Suitable initiators include ammonium persulfate, sodium persulfate, potassium persulfate, 2,2'-azobis(N,N'-dimethylencisobutyramidine) dihydrochloride, azo initiators, redox couples like persulfate-bisulfate, persulfate-ascorbic acid, and other suitable redox initiators. In certain examples, to reduce the potential for premature polymerization which may clog the emulsification system, addition of the initiator to the monomer phase may be just after or near the end of emulsification.

Photoinitiators present in the aqueous phase may be at least partially water soluble and may comprise between about 0.05% and about 10%, and in certain examples between about 0.2% and about 10% by weight of the oil phase. Lower amounts of photoinitiator allow light to better penetrate the HIPE foam, which can provide for polymerization deeper into the HIPE foam. However, if polymerization is done in an oxygen-containing environment, there should be enough photoinitiator to initiate the polymerization and overcome oxygen inhibition. Photoinitiators can respond rapidly and efficiently to a light source with the production of radicals, cations, and other species that are capable of initiating a polymerization reaction. The photoinitiators used to form foams within contemplation of the present disclosure may absorb UV light at wavelengths of from about 200 nanometers (nm) to about 800 nm, in certain examples from about 200 nm to about 350 nm, and in certain examples from about 350 nm to about 450 nm. If the photoinitiator is in the aqueous phase, suitable types of water-soluble photoinitiators include benzophenones, benzils, and thioxanthones. Examples of photoinitiators include 2,2'-Azobis[2-(2-imidazolin-2-yl)propane]dihydrochloride; 2,2'-Azobis[2-(2-imidazolin-2-yl)propane]disulfate dehydrate; 2,2'-Azobis(1-imino-1-pyrrolidino-2-ethylpropane) dihydrochloride; 2,2'-Azobis[2-methyl-N-(2-hydroxyethyl) propionamide]; 2,2'-Azobis(2-methylpropionamidine) dihydrochloride; 2,2'-dicarboxymethoxydibenzalacetone, 4,4'-dicarboxymethoxydibenzalacetone, 4,4'-dicarboxymethoxydibenzalcyclohexanone, 4-dimethylamino-4'-carboxymethoxydibenzalacetone; and 4,4'-disulphoxymethoxydibenzalacetone. Other suitable photoinitiators that can be used are listed in U.S. Pat. No. 4,824,765.

In addition to the previously described components other components may be included in either the aqueous or oil phase of a HIPE. Examples include antioxidants, for example hindered phenolics, hindered amine light stabilizers; plasticizers, for example dioctyl phthalate, dinonyl sebacate; flame retardants, for example halogenated hydrocarbons, phosphates, borates, inorganic salts such as antimony trioxide or ammonium phosphate or magnesium hydroxide; dyes and pigments; fluorescers; filler particles, for example starch, titanium dioxide, carbon black, or calcium carbonate; fibers; chain transfer agents; odor absorbers, for example activated carbon particulates; dissolved polymers; dissolved oligomers; and the like.

HIPE foam is produced from the polymerization of the monomers comprising the continuous oil phase of a HIPE. In certain examples, a HIPE foam layer may have one or more sublayers, and may be either homogeneous or heterogeneous polymeric open-celled foams. Homogeneity and heterogeneity relate to distinct layers within the same HIPE foam, which are similar in the case of homogeneous HIPE foams or which differ in the case of heterogeneous HIPE foams. A heterogeneous HIPE foam may contain at least two distinct sublayers that differ with regard to their chemical composition, physical properties, or both; for example layers may differ with regard to one or more of foam density, polymer composition, specific surface area, or pore size (also referred to as cell size). For example, for a HIPE foam, if the difference relates to pore size, the average pore size in the respective sublayers may differ by at least about 20%, in certain examples by at least about 35%, and in still other examples by at least about 50%. In another example, if the differences in the sublayers of a HIPE foam layer relate to density, the densities of the layers may differ by at least about 20%, in certain examples by at least about 35%, and in still other examples by at least about 50%. For instance, if one layer of a HIPE foam has a density of 0.020 g/cc, another layer may have a density of at least about 0.024 g/cc or less than about 0.016 g/cc, in certain examples at least about 0.027 g/cc or less than about 0.013 g/cc, and in still other examples at least about 0.030 g/cc or less than about 0.010 g/cc. If the differences between the layers are related to the chemical composition of the HIPE or HIPE foam, the differences may reflect a relative amount difference in at least one monomer component, for example by at least about 20%, in certain examples by at least about 35%, and in still further examples by at least about 50%. For instance, if one sublayer of a HIPE or HIPE foam is composed of about 10% styrene in its formulation, another sublayer of the HIPE or HIPE foam may be composed of at least about 12%, and in certain examples of at least about 15%.

A HIPE foam layer structured to have distinct sublayers formed from differing HIPEs may provide a HIPE foam layer with a range of desired performance characteristics. For example, a HIPE foam absorbent layer comprising first and second foam sublayers, wherein a first wearer-facing sublayer has a relatively larger pore or cell size, than the second sublayer, may more quickly absorb incoming fluids than the second sublayer. The first foam sublayer may be overlaid and be adjacent/continuous with or otherwise in contact with the second foam sublayer having relatively smaller pore sizes, and the second sublayer which exert greater capillary pressure and draw the acquired fluid from the first foam sublayer, restoring the first foam sublayer's ability to acquire more fluid. HIPE foam pore sizes may range from 1 to 200 μm and in certain examples may be less than 100 μm. HIPE foam layers of the present disclosure having two major parallel surfaces may be from about 0.5 to about 10 mm thick, and in certain examples from about 2 to about 10 mm. The desired thickness of a HIPE foam layer will depend on the materials used to form the HIPE foam layer, the speed at which a HIPE is deposited on a belt, and the intended use of the resulting HIPE foam layer.

The HIPE foam layers of the present disclosure may be manufactured to be relatively open-celled. This refers to a structure in which the individual cells or pores of the HIPE foam layer are in substantially unobstructed communication with adjoining cells. The cells in such substantially open-celled HIPE foam structures have intercellular openings or windows that are large enough to permit ready fluid transfer from one cell to its adjacent cells within the HIPE foam structure. For purpose of the present disclosure, a HIPE foam is considered "open-celled" if at least about 80% of the cells in the HIPE foam that are at least 1 μm in size are in fluid communication with at least one adjoining cell.

In addition to being open-celled, in certain examples HIPE foams are sufficiently hydrophilic to permit the HIPE foam to absorb aqueous fluids, for example the internal surfaces of a HIPE foam may be rendered hydrophilic by residual hydrophilizing surfactants or salts left in the HIPE foam following polymerization, by selected post-polymerization HIPE foam treatment procedures (as described hereafter), or combinations of both.

In certain examples, for example when used to form an absorbent layer, a HIPE foam layer may be flexible and exhibit an appropriate glass transition temperature (Tg). The Tg represents the midpoint of the transition between the glassy and rubbery states of the polymer. In general, HIPE foams that have a higher Tg than the temperature of use can be suitably strong but will also be relatively rigid and potentially prone to fracture. In certain examples, regions of the HIPE foams of the current disclosure which exhibit either a relatively high Tg or excessive brittleness will be discontinuous. Since these discontinuous regions will also generally exhibit high strength, they can be prepared at lower densities without compromising the overall strength of the HIPE foam.

HIPE foams intended for applications requiring flexibility should contain at least one continuous region having a Tg as low as possible, so long as the overall HIPE foam has acceptable strength at in-use temperatures. In certain examples, the Tg of this region will be less than about 40° C. for foams used at about ambient temperature conditions, in certain other examples less than about 30° C. For HIPE foams used in applications wherein the use temperature is higher or lower than ambient, the Tg of the continuous region may be no more than 10° C. greater than the use temperature, in certain examples the same as use temperature, and in further examples about 10° C. less than use temperature wherein flexibility is desired. Accordingly, monomers are selected as much as possible that provide corresponding polymers having lower Tg's.

HIPE foams useful for forming absorbent layers and/or sublayers within contemplation of the present disclosure, and methods for their manufacture, also include but are not necessarily limited to those foams and methods described in U.S. Pat. Nos. 10,045,890; 9,056,412; 8,629,192; 8,257,787; 7,393,878; 6,551,295; 6,525,106; 6,550,960; 6,406,648; 6,376,565; 6,372,953; 6,369,121; 6,365,642; 6,207,724; 6,204,298; 6,158,144; 6,107,538; 6,107,356; 6,083,211; 6,013,589; 5,899,893; 5,873,869; 5,863,958; 5,849,805; 5,827,909; 5,827,253; 5,817,704; 5,817,081; 5,795,921; 5,741,581; 5,652,194; 5,650,222; 5,632,737; 5,563,179; 5,550,167; 5,500,451; 5,387,207; 5,352,711; 5,397,316; 5,331,015; 5,292,777; 5,268,224; 5,260,345; 5,250,576; 5,149,720; 5,147,345; and US 2005/0197414; US 2005/0197415; US 2011/0160326; US 2011/0159135; US 2011/0159206; US 2011/0160321; and US 2011/0160689.

As reflected in FIG. 1, the absorbent layer formed of HIPE foam may include one or more patterns of perforations 42, including at least a first pattern disposed within an expected discharge region overlying the intersection of longitudinal and lateral axes 100, 200 of the pad. Perforations 42 may be punched, cut or otherwise formed through the entire z-direction depth of the HIPE foam absorbent layer, or only through a wearer-facing layer or partially into the wearer-facing portion thereof. When a HIPE foam absorbent layer is disposed directly beneath a topsheet as described herein, with no intervening acquisition layer formed of another material, perforations 42 may serve as a group of reservoirs to receive, temporarily hold, and aid in distributing rapid discharges of relatively small quantities of menstrual fluid, until the HIPE foam has sufficient time to distribute and absorb the fluid via capillary action. Additionally, such perforations help decrease bending stiffness of the absorbent layer, which may help increase both comfort and foldability. A more detailed description of configurations of such perforations in combination with examples of suitable absorbent layers may be found in U.S. Pat. No. 8,211,078.

Backsheet

The backsheet 30 may be positioned adjacent an outward-facing surface of the absorbent layer 40 and may be joined thereto by any suitable attachment methods. For example, the backsheet 30 may be secured to the absorbent layer 40 by a uniform continuous layer of adhesive, a patterned layer of adhesive, or an array of separate lines, spirals, or spots of adhesive. Alternatively, the attachment method may include heat bonds, pressure bonds, ultrasonic bonds, dynamic mechanical bonds, or any other suitable attachment mechanisms or combinations thereof. In other examples, it is contemplated that the absorbent layer 40 is not joined directly to the backsheet 30.

The backsheet 30 may be impervious, or substantially impervious, to liquids (e.g., urine, menstrual fluid) and may be manufactured from a thin plastic film, although other flexible liquid impervious materials may also be used. As used herein, the term "flexible" refers to materials which are compliant and will readily conform to the general shape and contours of the human body. The backsheet 30 may prevent, or at least substantially inhibit, fluids absorbed and contained within the absorbent layer 40 from escaping and reaching articles of the wearer's clothing which may contact the pad 10 such as underpants and outer clothing. However, in some instances, the backsheet 30 may be made and/or adapted to permit vapor to escape from the absorbent layer 40 (i.e., the backsheet may be made to be breathable), while in other instances the backsheet 30 may be made so as not to permit vapors to escape (i.e., it may be made to be non-breathable). Thus, the backsheet 30 may comprise a polymeric film such as thermoplastic films of polyethylene or polypropylene. A suitable material for the backsheet 30 is a thermoplastic film having a thickness of from about 0.012 mm (0.5 mil) to about 0.051 mm (2.0 mils), for example. Any suitable backsheet known in the art may be utilized with the present invention.

Some suitable examples of backsheets are described in U.S. Pat. Nos. 5,885,265; 4,342,314; and 4,463,045. Suitable single layer breathable backsheets for use herein include those described for example in GB A 2184 389; GB A 2184 390; GB A 2184 391; U.S. Pat. Nos. 4,591,523, 3,989,867, 3,156,242; WO 97/24097; U.S. Pat. Nos. 6,623,464; 6,664,439 and 6,436,508.

The backsheet may have two layers: a first layer comprising a vapor permeable aperture-formed film layer and a second layer comprising a breathable microporous film layer, as described in U.S. Pat. No. 6,462,251. Other suitable examples of dual or multi-layer breathable backsheets for use herein include those described in U.S. Pat. Nos. 3,881,489, 4,341,216, 4,713,068, 4,818,600; EP 203 821, EP 710 471; EP 710 472, and EP 0 793 952.

Folding

Referring to FIGS. 1, 3 and 4A-4C, a particular folding arrangement for the pad, to be placed inside an individual package, may be employed. This folding arrangement can be facilitated in some circumstances by construction of a thin pad utilizing an open-cell foam HIPE material for the absorbent layer, as described above. Open-celled HIPE foam provides advantages that include a thin and highly foldable but still suitably absorbent layer. It has been discovered that an absorbent layer of open-celled HIPE foam has greater resiliency and thereby enables a pad to take on less "set" from folding, than a pad having an absorbent layer of other absorbent materials that may cellulosic fiber and absorbent gelling material (or superabsorbent polymer material). Consequently, an absorbent layer formed of HIPE foam will more easily and completely return toward its open, flattened configuration following unpackaging and unfolding. It has been learned that this feature is desired by users because it reduces effort needed to manipulate the pad for positioning within the underpants. Further, the resiliency of the absorbent layer and the material forming it helps ensure that fluid transfer within the absorbent layer and along its length will be less likely to be interrupted or obstructed by permanently compressed/deformed regions created by folding, along the fold lines.

It has been learned, further, that this folding arrangement may be further facilitated and improved by the two-layer HIPE foam structure described above (and pictured in FIG. 2B, with a relatively larger-celled wearer-facing layer 40*a* and a relatively smaller-celled outward-facing layer 40*b*). Without intending to be bound by theory, it is believed that a relatively smaller-celled HIPE foam in an outward-facing layer 40*b*, having a greater number and density of cell walls and struts, has greater tensile strength needed to withstand the stress imposed on the outsides of the lateral folds (as described below) without substantial damage, while the relatively larger-celled wearer-facing layer 40*a*, having a lesser number and density of cell walls and struts, has greater compressibility and is more amenable to being compressed on the insides of the lateral folds. In other examples, an absorbent structure formed of or including a heterogeneous mass or layer assembly that includes a combination of relatively open-celled foam, such as but not limited to HIPE foam, in one or a plurality of discrete sections or pieces, layered and/or intermingled with fibers of a nonwoven web such that these components are present in a singularized layer, may provide a highly flexible, thin, foldable absorbent structure that substantially retains its fluid distribution and absorbency properties despite being folded as described herein. Non-limiting examples of such layer assemblies and/or heterogeneous masses are described in, for example, U.S. applications. Ser. Nos. 14/704,110; 15/343,989; 15/344,050; 15/344,177; 15/344,239; 15/344,255; 15/587,455; and Ser. No. 15/587,876; and U.S. App. Pub. No. US 2019/0269564.

As depicted in the figures, pad 10 may first be folded about side longitudinal fold lines 204, about which wings 15 are folded laterally over the wearer-facing surface of the pad. Following such folding, one or more suitably-sized section(s) of a thin release film or paper (not shown) may be laid over and applied to the portions of the wings having PFA deposits 35 thereon, to cover the adhesive and protect it from unwanted sticking, until the time the user wishes to apply the pad to her underpants. To avoid unnecessarily adding caliper to the pad in the completely folded configuration, it may be desired to avoid folding the pad along any longitudinal fold lines that traverse the absorbent layer or polymeric foam material included in the absorbent layer. As noted above, the central outward-facing surfaces of the pad having PFA deposits 35 thereon may also be covered with one or more sections of release film or paper (not shown).

After folding of the wings 15 about side longitudinal fold lines 204, the pad may be further folded into at least four sections including front section 210, front-mid section 211, rear-mid section 212 and rear section 213, along at least a front lateral fold line 201, middle lateral fold line 202 and rear lateral fold line 203. Middle lateral fold line 202 may, but does not necessarily have to, coincide with pad lateral axis 200. Sections 210, 211, 212 and 213 may be approximately equal in length, or the lengths of each (i.e., the positions of the lateral folding lines) may be adjusted to facilitate folding of one section length inside another section length.

Along lateral folding lines 201, 202 and 203, the pad may be folded into at least four sections 210, 211, 212 and 213 in a number of ways. However, for dual, but unrelated, purposes of (1) providing a folded pad configuration 10*a* with a singularized fold nose 214, and (2) minimizing folding damage to an absorbent layer formed of two layers of open-celled HIPE foam material as described above, one of two folding configurations may be applied.

Figure 4A:
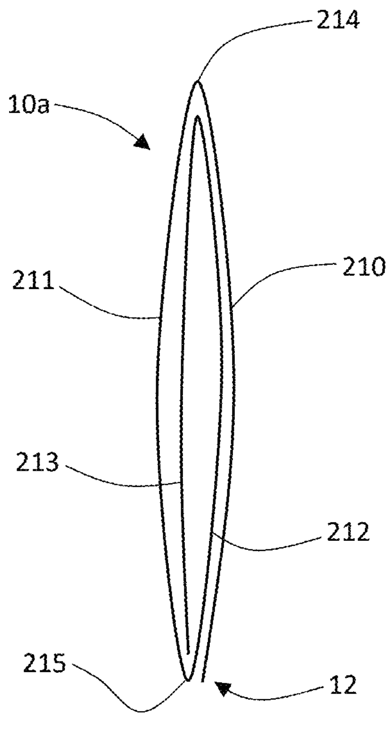
FIG. 4A is a schematic side view of a feminine hygiene pad folded in four sections in a roll fold configuration, with a main fold nose oriented toward the top of the figure.

The first is a "roll" fold configuration depicted in FIG. 4A. In a roll fold configuration, rear section 213 is folded along about rear lateral fold line 203 over rear-mid section 212; then both sections 213 and 212 together are folded about middle lateral fold line 202 over front-mid section 211; and lastly, the three section 213, 212 and 211 together are folded about front lateral fold line 201 over front section 210. The foregoing procedure results in a front-section-out roll fold configuration, in which front section 210 and forward end 12 are disposed on the outside of the folded pad configuration 10*a* as shown in FIG. 4A. It will be appreciated that an alternative roll fold configuration as described above may be formed by first folding the front section 210 over about front lateral fold line 201, and preceding to fold rearward, resulting in a rear-section-out roll fold configuration, in which rear section 210 and rearward end 14 lie on the outside of the folded configuration. A front-section-out roll fold configuration as shown in FIG. 4A may be desired, however, for purposes of user convenience, because it provides for front-to-rear unfolding that may be more intuitive for the user. It will be appreciated that a front-section-out roll fold configuration, or a rear-section-out roll fold configuration (if desired), may be created via steps that differ from those described above.

Figure 4B:
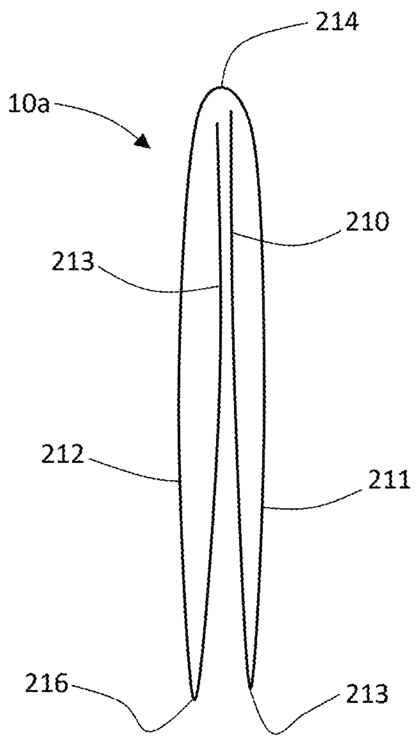
FIG. 4B is a schematic side view of a feminine hygiene pad folded in four section in a book jacket fold configuration, with a main fold nose oriented toward the top of the figure.
Figure 4C:
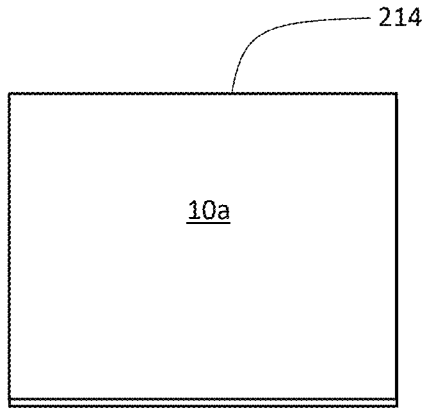
FIG. 4C is a schematic front view of a folded feminine hygiene pad, with a main fold nose oriented toward the top of the figure.

The second configuration is a "book jacket" fold configuration, named herein because it resembles the manner in which a book jacket (or book dust jacket) is folded, and is depicted in FIG. 4B. In a book jacket fold configuration, front section 210 is folded about front lateral fold line 201 over front-mid section 211; and rear second 212 is folded about rear lateral fold line 203 over rear-mid section 212 (these two folds can occur simultaneously or one after another in either order). Finally, the two remaining portions comprising front section 210 folded over front-mid section 211 as one portion, and rear section 213 folded over rear-mid section 212, are folded about middle lateral fold line 202 to bring them together to create the book jacket fold configuration depicted in FIG. 4B.

It will be appreciated that in both the roll and book jacket fold configurations depicted and described, in all folds about lateral fold lines 201, 202 and 203, the fold is formed with the wearer-facing (i.e., topsheet) surfaces facing inward in the fold. This serves three purposes. First, it is believed that it provides for more intuitive, and therefore more convenient, unfolding for the user. Second, it cooperates with an absorbent layer formed of two sublayers of open-celled HIPE foam, as described above, to help minimize permanent deformation, or damage, to the absorbent layer resulting from folding.

Third, it can be seen in FIGS. 4A and 4B that both the roll fold configuration and the book jacket fold configuration result in an isolated and singularized main fold nose 214, wherein an outside folded edge along one of the lateral fold lines is alone, with no proximate folded or end edges present—in contrast to the secondary fold nose 215 proximate to end edge 12 shown at the bottom of FIG. 4A and proximate secondary fold noses 216, 217 shown at the bottom of FIG. 4B). A singularized main fold nose 214 may be desired for purposes of user convenience and user perceptions of greater imperviousness to contamination of the product, as will be described below.

Package

Figure 5A:
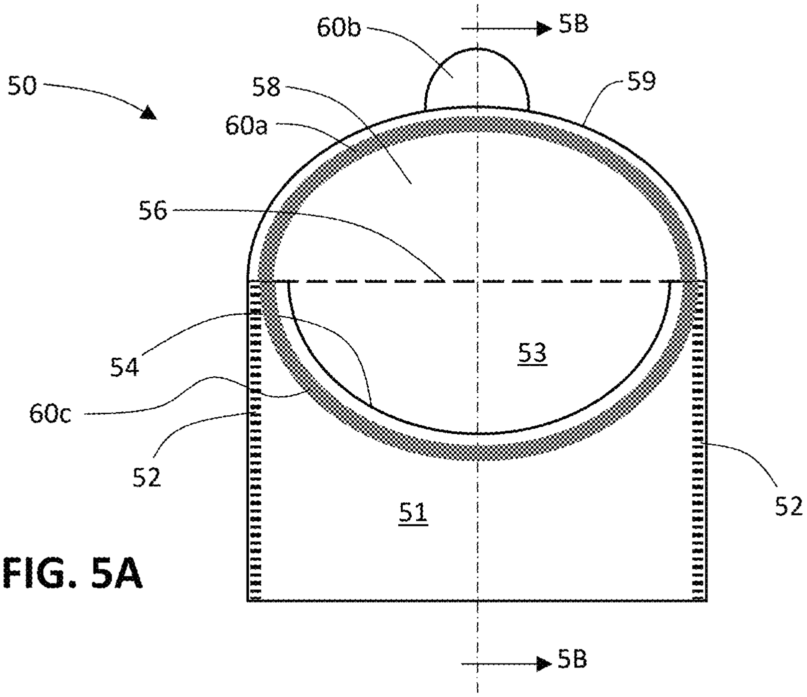
FIG. 5A is a front view of an envelope package in an opened configuration.
Figure 5B:
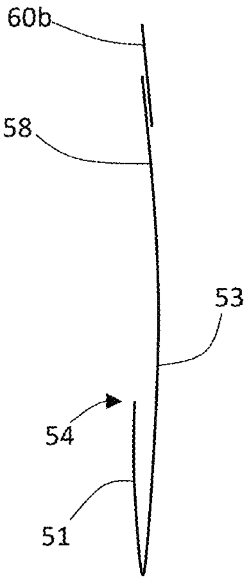
FIG. 5B is a schematic cross section of the package as shown in FIG. 5A, taken along line 5B-5B in FIG. 5A.
Figure 6A:
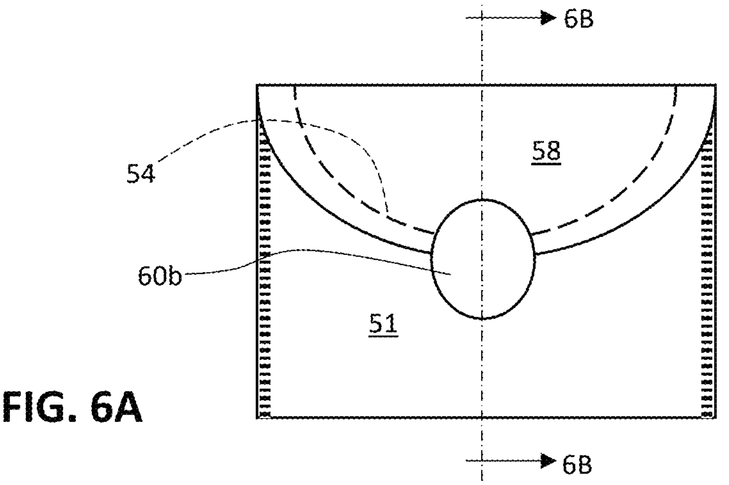
FIG. 6A is a front view of an envelope package in a closed configuration.
Figure 6B:
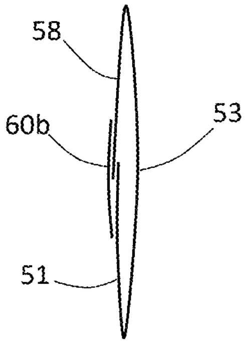
FIG. 6B is a schematic cross section of the package as shown in FIG. 6A, taken along line 6B-6B in FIG. 6A.
Figure 7:
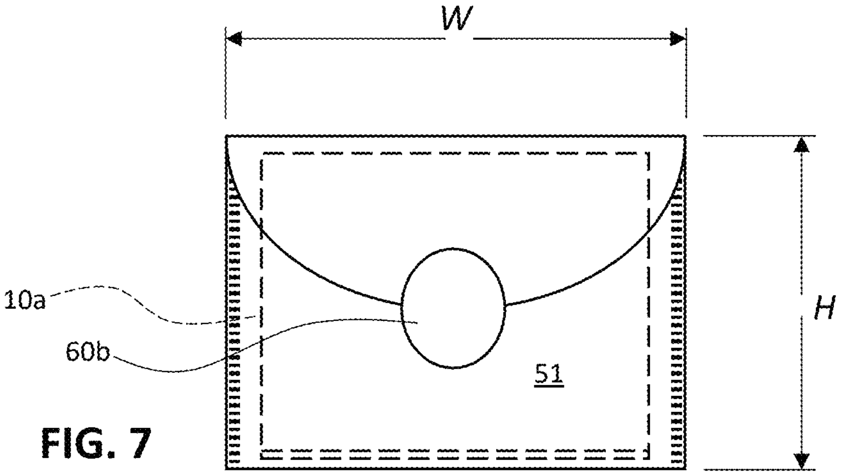
FIG. 7 is a front view of the closed envelope package as shown in FIG. 6A, showing positioning of a folded feminine hygiene pad within the package.

Referring to FIGS. 5A, 5B, 6A, 6B, 7 and 8, for purposes of providing a package for an individual folded feminine hygiene pad that can be easily and quietly opened by a user, it may be desired to provide a package having some or all of the features depicted and described herein. Package 50 may have an envelope configuration as depicted. It may be formed from a single sheet of web material, preferably a nonwoven web material, polymeric film material, or laminate of a nonwoven web material and polymeric film material. The single sheet of material may be cut to appropriate length, size and shape configured to provide front panel 51, rear panel 53 and opening flap 58, wherein front panel 51 is cut to provide an extended access front opening edge 54 visible in an opened configuration shown in FIGS. 5A and 5B, and an opening flap 58 that may in some examples be configured to overlie and cover front opening edge 54 when in the closed configuration as shown in FIGS. 6A and 6B (flap 58 folded about opening flap fold line 56). The cut package material may be folded as shown and then ultrasonically, thermally, compressively and/or adhesively bonded alongside edges thereof to form side seams 52 and thereby form the envelope structure. In order to minimize the size of the package, it may be desired to minimize the margin of film material along the side seams that is present in the seams, and utilize a thermal bonding-fusion mechanism (e.g., by application of heat directly, or via ultrasonic means) that results in side seams formed of welded/fused film material that are no more than 6 mm in width, more preferably no more than 4 mm in width, and even more preferably no more than 3 mm in width.

Where the package includes a polymeric film material, it may be desired that the film material have properties that make it relatively quiet when handled or manipulated, for purposes of providing a discreet package. In some examples, the film material may comprise polyethylene. In some examples the polymer resin from which the film is formed may include a particle filler or additive, such as particles of calcium carbonate. Without intending to be bound by theory, it is believed that such particle fillers may beneficially reduce noise generation/transmission characteristics of the polymer film. Nonlimiting examples of suitable polymer film and particle filler compositions are disclosed in US 2015/0376384 and US 2015/0376383.

Many currently marketed feminine hygiene pads are individually packaged in packages that require the consumer to destructively tear the package along seams or through the package material itself, to access the pad within. Such destructive opening creates the potential to generate, or actually generates, unwanted noise during package opening. In order to further minimize noise created by opening of the package, and to preserve the package structure so it can be used to receive and hold a used pad for later disposal, it may be desired that the package be configured so that it can be opened without substantial destruction thereto. In some examples, the packaging may be configured such that accessing the pad within requires separating the package material along a total/combined distance of no more than 50 percent of the total length of all seams present, more preferably no more than 30 percent of the total length of all seams present, and even more preferably no more than 15 percent of the total length of all seams present.

In some examples, an openable closure element may be provided, in combination with any of the other package features described herein. In some examples a closure element may include a releasable flap closure adhesive 60*a* on the underside of the flap 58, or panel closure adhesive 60*c* on the outside of the package front panel 51, and in some examples may include an adhesive closure tape or sticker 60*b* that overlies the edge of opening flap 58 and adheres to the front panel 51 of package 50. In some examples the closure element may be a deposit of releasable closure adhesive 60*a* (e.g., in a position as depicted in FIG. 5A) alone, applied to the underside of flap 58 in a suitable position and shape to adhere the flap to front panel 51 without contacting a pad contained in the package. Such adhesive may be applied in a position on the flap so as to be present along most or substantially the entire opening edge 54 when the flap 58 is closed (i.e., extending substantially along the flap edge and/or opening edge 54 from one side seam 52 to the other), to make a more complete closure that reduces chances of contamination of a new pad within the package. In some examples a deposit of releasable panel closure adhesive 60*c* may be disposed on the front panel 51, which may be desired to minimize likelihood of inadvertent contact with the pad. In some examples the releasable adhesive may also be reusable/refastenable, which may make the package 50 more useful for storing a used pad for disposal.

Figure 9A:
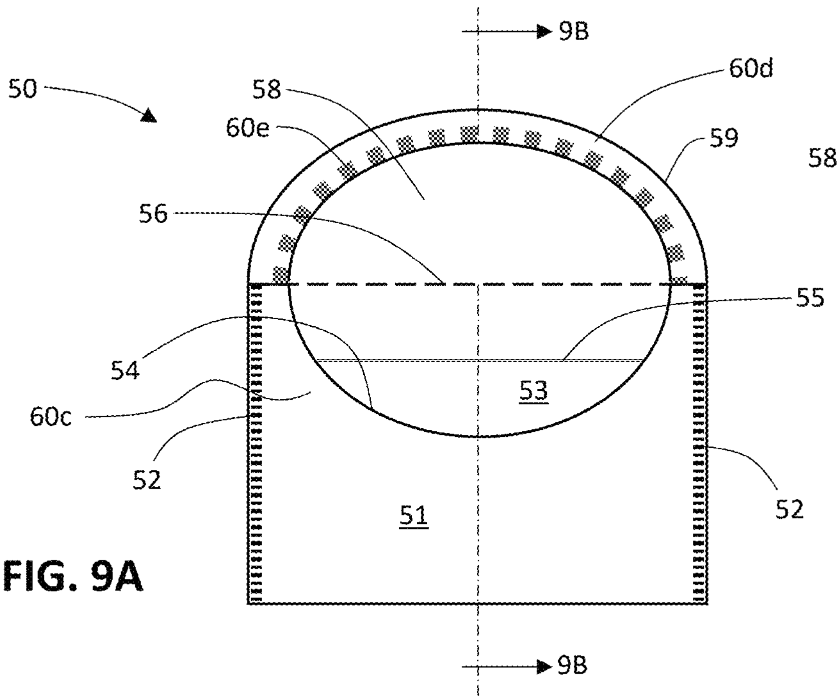
FIG. 9A is a front view of another example of an envelope package in an opened configuration.
Figure 9B:
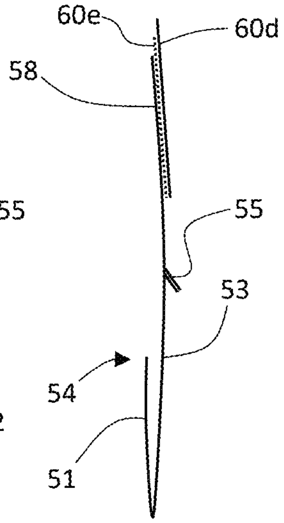
FIG. 9B is a schematic cross section of the package as shown in FIG. 9A, taken along line 9B-9B in FIG. 9A.
Figure 10A:
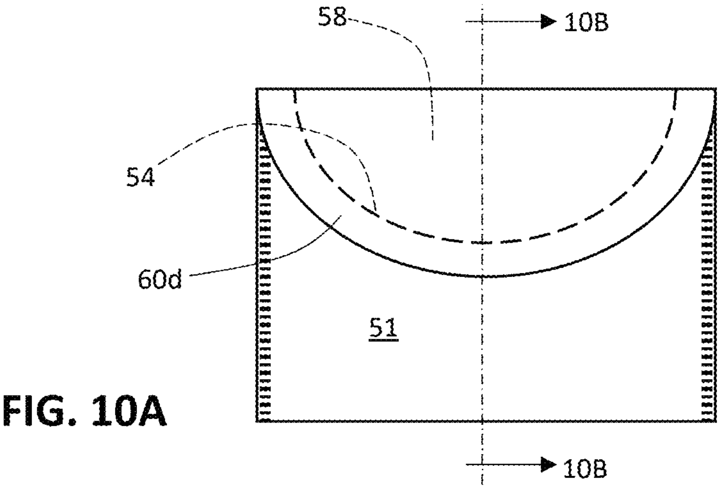
FIG. 10A is a front view of an another example of an envelope package in a closed configuration.
Figure 10B:
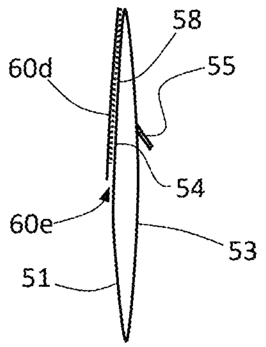
FIG. 10B is a schematic cross section of the package as shown in FIG. 10A, taken along line 10B-10B in FIG. 10A.

In some examples such as depicted in FIGS. 9A, 9B, 10A and 10B, an envelope package may be formed about a pad in a flow-wrap process in which a seam 55 is created in back panel 53. As depicted in FIGS. 9B and 10B, scam 55 is a fin seam; however, scam 55 may also be in the form of an overlap seam that lies flush along the rear panel 53. Either a fin scam or an overlap seam may be formed and held together via thermal bonding/fusion of the separate portions of film joined therealong, by a deposit of a suitable adhesive between the separate portions of film, or a combination thereof. In some examples it may be desired that attachment between the joined sections forming back panel 53, at seam 55, whether effected by adhesive or by welding/fusion, be intermittent or discontinuous and may have spaced intervals of attachment, rather than being continuous, along seam 55. This may be desired to allow venting of air from the finished package upon compression of the package, such as may occur in processes downstream of package formation, reducing chances that the package will burst open along seams or along the flap closure.

Still referring to FIGS. 9A, 9B, 10A and 10B, rather than be separate of film forming front panel 51, flap 58 may be contiguous and integral with film forming front panel 51, and may be defined along edge 54 by a path of perforations, laser scoring, mechanical scoring or cutting or other suitable mechanism for imparting a path of separation along which front panel 51 and flap 58 will easily tear away or separate from each other. A larger flap sticker 60*d* with flap sticker adhesive 60*c* disposed to hold it to the front panel 51 and flap 58 may overlie the path of separation and thereby prevent opening of the package until desired by the user. When the user wishes to open the package, she may lift and peal the flap sticker 60*d* upwardly, and the adhered flap sticker 60*d* will pull the flap 58 along therewith, causing the front panel 51 and flap 58 to separate along the path of separation to create access opening edge 54. In some examples the film forming front panel 51 may be cut (such as by die-cutting) substantially entirely through its thickness along the path of separation during the manufacturing/packaging process, following application of flap sticker 60*d* to the package film, such that the flap sticker 60*d* and flap sticker adhesive 60*e* thereunder are the only structure that effectively holds the flap in a closed position after packaging is completed. This may provide for a particularly quiet flap opening experience for the user, when a suitable flap sticker adhesive composition is included, because the user will not need to tear the film of the front panel (which has a potential to generate noise) to open the package. In some examples it may be desired that the flap sticker be of a size and shape suitable to cover the entirety of the path of separation. Such a feature may serve to enhance the ability of the package to protect a new pad from contamination prior to use; to create favorable consumer perceptions resulting from such effect; and to make the package a more effective container/disposal aid for receiving, isolating and carrying a used pad until the time the user can dispose of it.

Figure 10C:
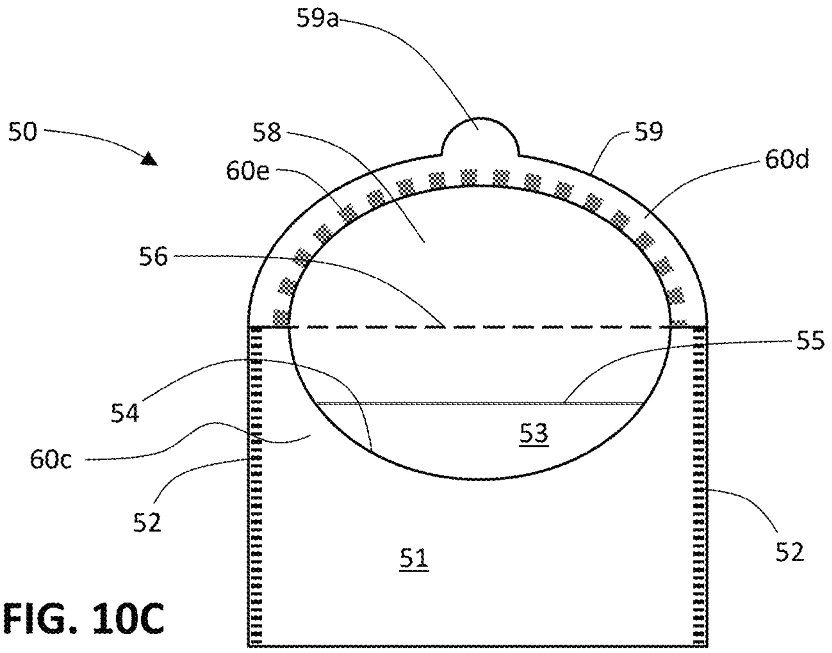
FIG. 10C is a front view of an another example of an envelope package in an opened configuration.
Figure 10D:
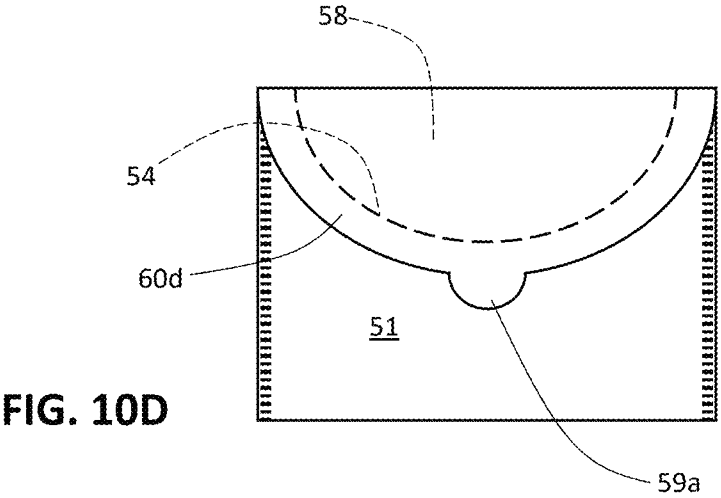
FIG. 10D is a front view of an another example of an envelope package in a closed configuration.

As may be appreciated from FIGS. 10C and 10D, in some examples a flap sticker 60*d* may include a lift tab 59. Lift tab 59 may simply be an extension of the distal end of flap sticker 60*d*. Lift tab 59 or a distal portion thereof may be provided with a reduced amount, or entirely without, any adhesive 60*e* thereon. In such configuration, lift tab 59 may easily be lifted away from front panel 51 and grasped by the consumer, facilitating the consumer's lifting and peeling upward of flap sticker 60*d* and/or flap 58 to open the package.

It will be appreciated that a package configuration such as any of those depicted in FIGS. 5A, 5B, 6A, 6B, 7, 8, 9A, 9B, 10A-10D and described herein, may be configured so as to be openable with substantially limited or even no destruction thereto, and to be recloseable, so as to make it suitable to serve as a disposal aid-into which the user may insert a used, folded pad, and reclose the package around it, to isolate the used pad until a convenient time for disposal thereof. Where an openable flap 58 is provided, it may be configured to be openable without substantial destruction of the flap itself, and without substantial destruction or separations of other portions of the package (e.g., side seams 52), such that the flap is effectively recloseable to cover the access opening. Additionally, a reclosure refastenability feature may be provided, such as, for example a releaseable/refastenable flap closure adhesive 60*a* beneath the flap or a releasable/refastenable adhesive 60*e* beneath a flap sticker 60*b* or 60*d*, such that the flap 58 and access opening may be fastenably reclosed after opening.

As may be appreciated from the figures, in some examples it may be desired that the opening edge 54 follow a curving path, which will avoid localization of stresses therealong and thereby avoid unintended tearing of the package film. In some examples it may be desired that the curving path be configured such that a greatest portion of the contained folded pad is exposed and made accessible to the user at a location between the side seams 52, for purposes of user convenience.

It may be desired that the package 50 be sized relative the folded pad 10*a*, so as to be as small as possible (for convenient and discreet carry) without being so snug as to create friction between the folded pad 10*a* and the insides of the package sufficient to frustrate easy and quiet withdrawal of the pad from the package. Similarly, and also for purposes of nondestructive and easy withdrawal of the pad from the package, it may be desired that the folded pad 10*a* and the package 50 be configured such that there are few or no substantial deposits of adhesive, preferably no deposits of adhesive, disposed between the outside surfaces of the folded pad 10*a* and the inside surfaces of the package 50 and/or the opening flap 58.

Through prototyping, it has been discovered that a normal-capacity daytime use feminine hygiene pad of the same design and materials as current ALWAYS INFINITY pads (a product of The Procter & Gamble Company, Cincinnati, Ohio) and having an absorbent layer formed of an open-celled HIPE foam, can be folded and packaged as described herein to have an uncompressed package caliper when laid flat on a horizontal surface of 25 mm or less, more preferably 20 mm or less, even more preferably 15 mm or less, or from 10 mm to 25 mm, more preferably from 10 mm to 20 mm, and even more preferably from 10 mm to 15 mm-following removal from a larger package containing a plurality of individually packaged pads, and a 24-hour rest period. This package caliper contributes to providing a relatively small packaged pad believed to be preferred by many consumers for its discreet pocketability and ease of discreet one-hand carry.

It has been discovered that, between packages that are square or nearly square in shape (aspect ratio of package height to width of approximately 1.0) and packages that are rectangular but not square in shape, consumers prefer the non-square packages, for reasons that are not thoroughly understood but are believed to relate to perceived convenience of pocketability and/or discreet carry. Accordingly, it may be desired to configure the pad and the package such that the closed package with the contained pad is rectangular in shape and has an aspect ratio of height H to width W (see FIG. 7) of 0.40 to 0.95, more preferably 0.45 to 0.85, and even more preferably 0.50 to 0.75.

Figure 8:
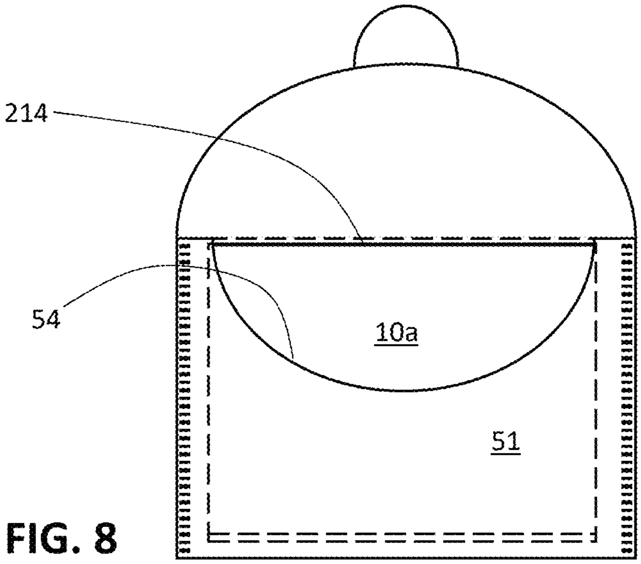
FIG. 8 is a front view of the closed envelope package as shown in FIG. 5A, showing positioning of a folded feminine hygiene pad within the package.

In order to maximize user convenience, it may be desired that a folded pad 10*a*, folded as described above, be placed within the package with a main fold nose 214 disposed closest the package opening or top of the package (when the package is in an opened configuration) as suggested in FIG. 8. Placing a main fold nose 214 relative the package opening in this orientation presents the user with a single edge of the folded product that she can quickly and easily visually and/or tactilely identify, for easy and quick grasping of the entire pad, e.g., between a thumb and forefinger, and removal from the package. By contrast, when multiple edges of the folded pad are presented in the opening, user effort grasping and removing the pad from the package may require more slightly more concentration and/or effort. It has been discovered that users substantially prefer the former configuration, for this reason, and also for the reason that users perceive that this configuration of the pad within the package makes the pad more impervious to contamination.

Another feature that may be desired to improve user convenience is to impart contrasting colors or other visible characteristics to the respective outside visible surfaces of the folded pad 10*a* and the inside surfaces of the package material, thereby providing a visual contrast between the inside surfaces of the opened package and an outer surface of the pad as contained therein, visible immediately after the package is opened. This feature helps the user quickly visually identify the pad within the package for grasping and removal. Visual contrast may be imparted by any suitable techniques including tinting, pigmenting or printing the materials of the pad backsheet, the release film or paper, the package material, or any combination thereof. Herein, a "visual contrast" between colors or shades of two respective materials means that an ordinary observer having 20/20 vision (natural or corrected) and no substantial color vision deficiency, in normal office lighting conditions appropriate for desktop work, can perceive a contrast between the color(s) on the outside of the folded pad in the package, and the color(s) of the inside of the package material, with the package in an opened condition. Alternatively, for relatively close colors or shades, a "visual contrast" is identified when the value of delta E* determined through the Visual Contrast method below is equal to or greater than 2.0. For enhanced visual contrast, it may be preferred that the value of delta E* be equal to or greater than 3.5. Alternatively, where decorative designs are visibly present on one or both the outside of the folded pad as contained in the package, and the inside of the package material with the package in opened configuration, a "visual contrast" is identified when a design is visibly present on one but not the other, or when designs are visibly present on each but the designs differ in any visible respect.

Process

Figure 11A:
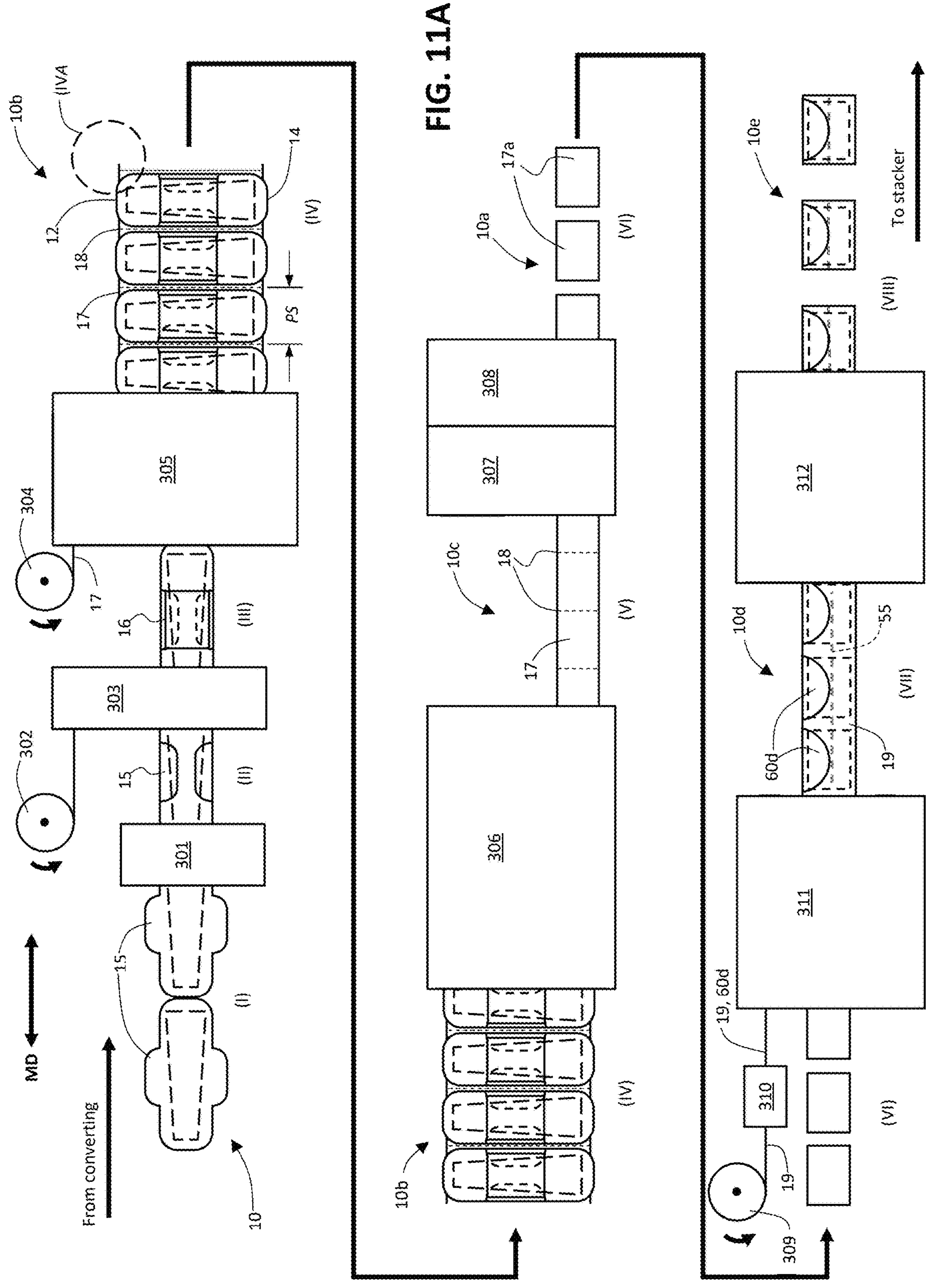
FIG. 11A is a schematic plan view depiction of an example of process flow for finishing and packaging feminine hygiene pads.

It has been learned that one or more of the process steps described below may be advantageous for imparting product features described above, and may provide additional advantages in manufacturing efficiency, reliability and quality assurance. Referring now to FIG. 11A, a process for manufacturing a packaged, folded feminine hygiene article is schematically depicted.

Starting at the top left of the figure, feminine hygiene pads 10 may be received from a converting line in configuration (I) in substantially finished condition, and with their longitudinal axes oriented in the machine direction MD. At the beginning of the process, pads 10 may have yet to have had PFA deposits 35 (see FIGS. 2A, 2B and 3) applied. Pads 10 may include wings 15, as previously described. Pads 10 may be conveyed from the converting line to a wing folding unit 301, which folds wings 15 (along, e.g., side longitudinal fold lines 204, see FIG. 1) over the wearer-facing/topsheet surfaces of the pads 10, from which they emerge in configuration (II) with the wings 15 folded over. (A more detailed example of a depiction of a pad as it would appear in configuration (II) appears in FIG. 3.)

In configuration (II), the pads may be conveyed to a wings coversheet application unit 303. The wings coversheet application unit 303 may be configured to receive wings coversheet stock from a supply roll 302 (which may be a roll of polymeric film or paper bearing an adhesive release surface or coating), cut it into individual wings coversheets 16, apply deposits of backsheet adhesive thereto, and place the individual wings coversheets 16 bearing the adhesive over the folded wings 15. Upon contact between the wings coversheet 16 and the folded over, outward-facing surfaces of the wings, the adhesive applied to the wings coversheet 16 can adhere and effectively transfer to the wings, so as to become a first portion of PFA deposit 35 disposed on the wings (see, e.g., FIGS. 2A and 3) and later remain in place on the wings when a user peels away the coversheet 16 in preparation to apply the pad to underwear. Prior to use, the wings coversheet 16 may serve to cover the adhesive and prevent it from being contaminated or adhering to surfaces not intended by the user. In some examples, the process may be configured to apply the adhesive directly to the wings directly/initially, rather than to the wings coversheets 16. The process can be configured such that the pads emerge from wings coversheet application unit 303 in configuration (III).

In configuration (III), the pads may be conveyed to a turn and repitch unit 305. Unit 305 may be a single unit, or a combination of cooperating units configured to receive individual pads moving with their longitudinal axes oriented in the machine direction MD, rotate them 90 degrees such that their longitudinal axes are oriented in the cross direction CD, phase them (i.e., space them along the MD by a predetermined distance), and place them onto a continuous web of PFA coversheet stock 17. Unit 305 may also be configured to receive PFA coversheet stock 17 from a supply roll 304 and place the rotated pads thereonto. Unit 305 may also be configured to apply a deposit of backsheet adhesive, either directly to the pads, or indirectly to the PFA coversheet 17 stock, such that the adhesive applied to the backsheet coversheets can adhere and effectively transfer to outward-facing surfaces of the pads (e.g., the outward-facing surfaces of the pad backsheets), so as to become a second portion of PFA deposit 35 disposed on the pads (see, e.g., FIGS. 2A and 3) and later remain in place on the pads when a user peels away the PFA coversheet 17 in preparation to apply the pad to underwear.

PFA coversheet stock 17 may be any polymeric film or paper material suitable for serving as a releasable coversheet for covering areas of the pad bearing PFA deposit(s) 35. Further, in many circumstances, it may be desired that coversheet stock 17 be a material that is quiet, i.e., does not generate substantial audible noise, when manipulated by a user (such as when she removes the PFA coversheet 17*a* from the pad in preparation to apply the pad to underwear). For this reason, a relatively quiet polymeric film may be selected for the coversheet stock 17. In some examples the film may be predominately polyethylene, of an average caliper no greater than 0.08 mm (80 μm), preferably no greater than 0.065 mm (65 μm) and even more preferably no greater than 0.05 mm (50 μm). Polyethylene-based films tend to be relatively quiet as compared with paper and with films based on other polymers. Other relatively quiet film materials might also be selected.

PFA coversheet stock 17 may be provided on the supply roll 304 with machine-direction-spaced separation perforations 18 already present, or alternatively, unit 305 may include a perforation unit (not specifically shown) that provides successive cross-direction lines of separation perforations 18 (or other suitable lines of weakness, such as scoring partially through the thickness of the PFA coversheet stock), substantially uniformly spaced along the machine direction by distances approximately corresponding to the widths of the pads with wings folded. Spacing PS of separation perforations 18 along the coversheet stock 17 may include any desired margins beyond the pad widths, but in some circumstances, it may be desired that such margins be minimized for purposes of compactness and neatness of the completed folded pad product. Thus, in some examples it may be desired that machine-direction spacing PS of separation perforations 18 be no greater than 125 percent of the average width of the pads (wings, if present, folded), more preferably no greater than 120 percent of the average width of the pads, and even more preferably no greater than 115 percent of the average width of the pads. As a result, following completion according to the further process steps described below, the widths of individual PFA coversheets 17*a* on the pad products will be, respectively, no greater than 125 percent of the average width of the pads (wings, if present, folded), more preferably no greater than 120 percent of the average width of the pads, and even more preferably no greater than 115 percent of the average width of the pads. It will be appreciated, however, that as a feature or result of the process steps described herein, in no case will the machine-direction spacing PS be less than 100 percent of the average width of the pads.

Additionally, in FIG. 11A, it can be observed that the individually oriented, spaced series of pads 10*b* in configuration (IV) may have, between them prior to folding, separation perforations 18 in the PFA coversheet stock 17. It may be appreciated that the above-described method and any variant thereof, that successively places pads 10 on backsheet coversheet stock with the pads' longitudinal axes oriented in the cross direction CD, enables the manufacturer to provide coversheet stock 17 having a cross-direction dimension that is less than the length ($L_P$, see FIG. 3) of the pads. To illustrate, referring to location (IVA) of FIG. 11A, it can be seen that coversheet stock 17 does not extend in the cross direction CD to the ends 12, 14 of the pads, but rather, lies short of them. This feature of the process is another way to enable the manufacturer to provide for a smaller, neater folded pad configuration because no unused margins of coversheet stock material 17 extend past the ends 12, 14 of the pads.

In configuration (IV), the series of pads 10*b* with adhered PFA coversheet stock 17 may be conveyed to a folding unit 306. Folding unit 306 may be configured to continuously fold the series of pads 10*b* into two, three, four or more sections (for example, along fold lines 201, 202, 203, 204; see FIGS. 3, 4A and 4B), resulting in a connected series of folded pads 10*c* (adhered to PFA coversheet stock 17), in configuration (V). Folding unit 306 may be configured such that in configuration (V), the connected series of folded pads 10*c* are imparted with, for example, one of the folding configurations schematically illustrated in FIGS. 4A and 4B.

In configuration (V), the connected series of folded pads 10*c* may be conveyed to a separation unit 307. Separation unit 307 may be configured to continuously and successively exert machine direction tensile force on the successive pads, perpendicular to and across the lines of the separation perforations 18, causing the PFA coversheet stock 17 to separate along the perforations 18. This results in a series of separated, folded pads 10*a*, each of which includes an individual PFA coversheet 17*a*. Following separation, the folded, separated pads may be conveyed to a packaging phasing unit 308 configured to space the folded pads apart from one another along the machine direction, by a predetermined distance suitably selected for individual packaging as will be described below.

Figure 12:
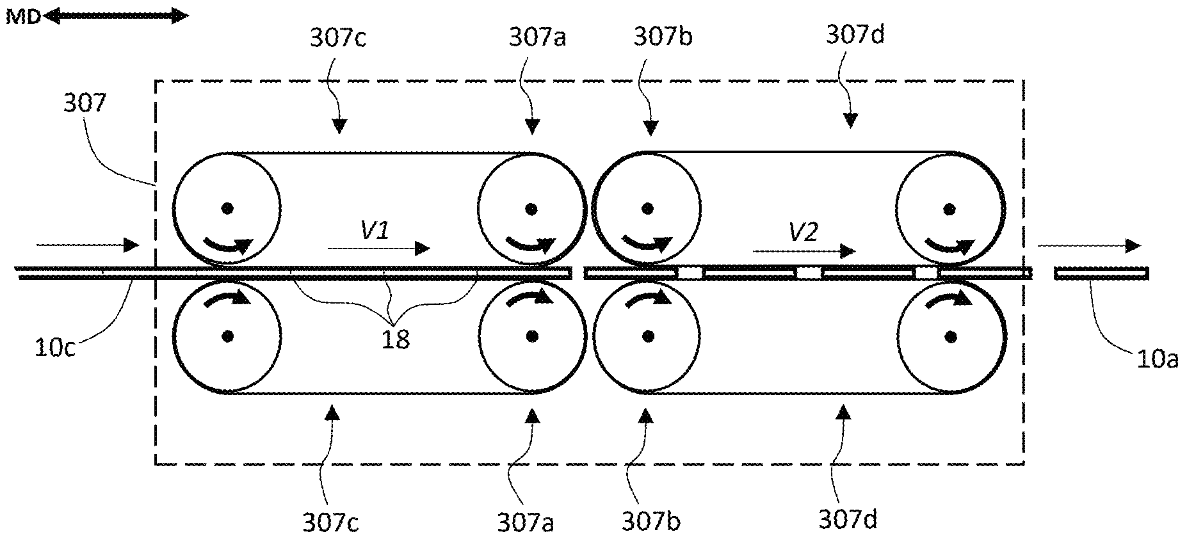
FIG. 12 is a schematic side view depiction of operating components of an example of a separation unit, shown operating with a series of folded pads.

In some examples, referring to FIG. 12, separation unit 307 may include two successive pairs of opposing separation rollers including an upstream pair 307*a* and a downstream pair 307*b*. Each respective pair of separation rollers 307*a*, 307*b* may be configured to operate without conveyor belts (whereby the pads 10*c*, 10*a* pass directly through the nip between each pair of rollers), or with respective corresponding, respective upstream and downstream pairs of upper and lower conveyor belts 307*c*, 307*d* cycling about each of the rollers (whereby the pads pass between the respective upper and lower belts). Upstream separation roller pair 307*a* may be operated such that their circumferential roller surfaces move at a tangential/linear velocity V1. Downstream separation roller pair 307*b* may be operated such that their circumferential roller surfaces move at a tangential/linear velocity V2. To effect separation of successive pads, the system may be configured and operated such that V2 is greater than V1. As each connected pad in the series 10*c* emerges from the nip or space between pair 307*a* and enters the nip or space between pair 307*b* moving at a greater velocity, friction between the pad and pair 307*b*, or between the pad and belts 307*d*, increases machine direction tension in the pad between roller pairs 307*a*, 307*b*, and causes each, leading, exiting folded pad 10*a* to separate from the incoming/trailing series of pads 10*c*, along the separation perforations 18.

From the foregoing description it will be appreciated that the average width of the PFA coversheets 17*a* on the separated folded pads 10*a* will be approximately equal to the spacing PS between the separation perforations 18 as shown in FIG. 11A. Thus, according to the description above, it may be desired that average width of the adhesive coversheets 17*a* be less than 125 percent, more preferably less than 120 percent, and even more preferably less than 115 percent (and in all cases at least 100 percent) of the width of the pads. For purposes of identifying presence of this feature and eliminating uncertainty resulting from variance in wing portion folding locations, the width of a pad is the greatest width of any portion of the absorbent layer 40 or absorbent core component disposed between the topsheet and backsheet. For purposes herein, averages may be calculated after measurements of adhesive backsheet coversheets and absorbent layer/core components of 10 examples of the product in question.

In view of the foregoing process description, the configuration of the separation perforations 18 may be important to efficient operation of the process as well as appearance of the resulting product. It may be desired that the separation perforations 18 through the coversheet stock 17 are not so extensive as to unacceptably compromise the tensile strength of the coversheet stock 17, i.e., its ability to withstand ordinary machine direction operating tension in the line upstream of the separation unit 307. If the separation perforations 18 are too extensive, the coversheet stock 17 may be vulnerable to premature, unwanted separation in processes upstream of the separation unit 307, which can necessitate line shutdown. On the other hand, it may be desired that the coversheet stock separate easily, neatly and cleanly in separation unit 307, so as to provide for smooth, even and uninterrupted conveyance of the pads through the separation unit 307 and the remainder of the line downstream, and provide a neat finished appearance to the separated side edges of the individual PFA coversheets 17*a*, such that the edges have a relatively smooth, not jagged appearance to the naked eye.

Figure 13A:
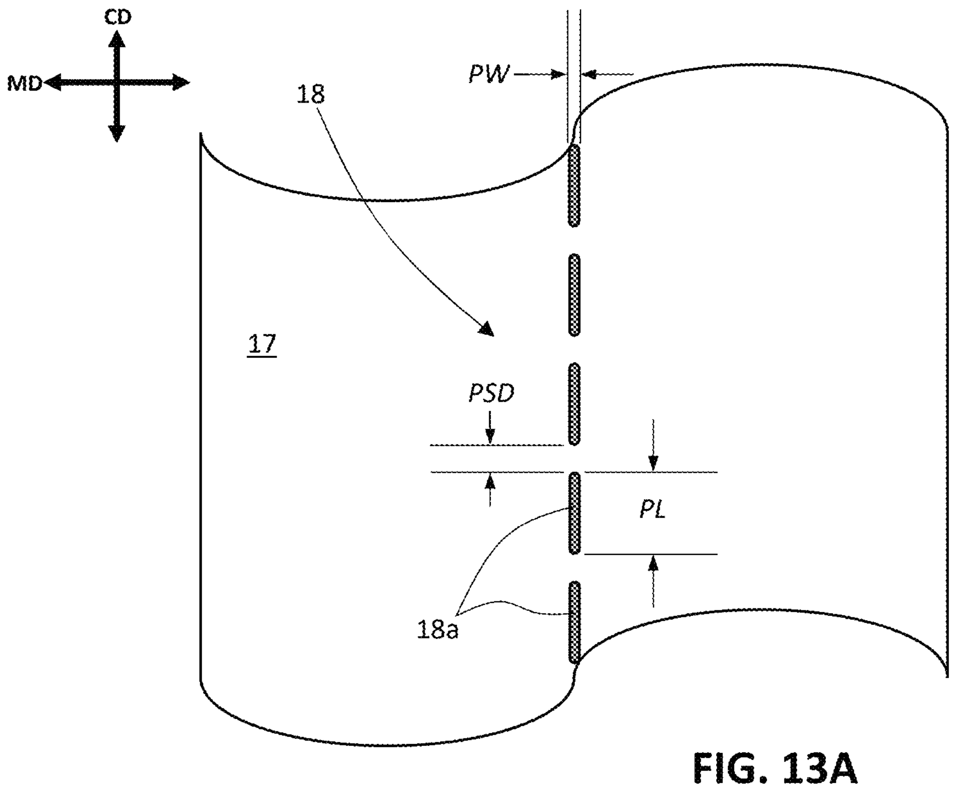
FIG. 13A is an expanded plan view depiction of a portion of PFA coversheet supply web with separation perforations.

Referring to FIG. 13A, separation perforations 18 may be substantially uniformly dimensioned and spaced to provide for smooth and even separation. The perforations may be created mechanically, e.g., by use of a perforating die, or thermally, e.g., by use of a suitably selected and tuned laser. The perforations may penetrate the film entirely, or only partially, to an extent sufficient to propagate an orderly separation of the file along the perforations. Separation perforations 18 have an average length PL in the cross direction CD, an average separation distance PSD in the cross direction CD, and an average perforation width PW in the machine direction MD. For purposes of balancing the needs for preserving suitable tensile strength in coversheet stock 17 upstream of the separation unit 307, providing for efficient separation of pads in separation unit 307, and providing for PFA coversheets 17*a* with neatly separated edges in the finished product, it may be desired to configure perforating equipment such that perforations 18 have the following ranges of dimensions and ratio:

average PL=0.4 mm to 3.5 mm; more preferably 0.45 mm to 2.0 mm; and even more preferably 0.5 mm to 1.0 mm;

average PSD=0.7 mm to 2.5 mm; more preferably 0.75 mm to 1.8 mm; and even more preferably 0.80 mm to 1.1 mm;

average PW=0.015 to 0.1 mm; and average PL/(average PL+average PSD)=0.15 to 0.70; more preferably 0.25 to 0.55; and even more preferably 0.30 to 0.50.

Figure 13B:
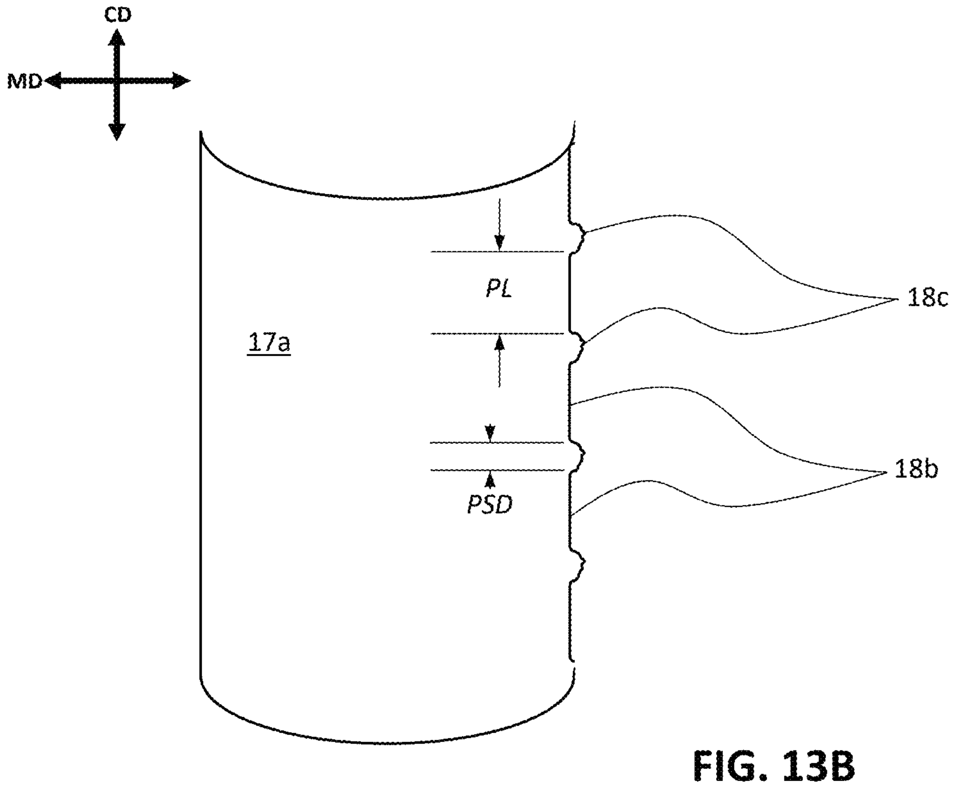
FIG. 13B is an expanded plan view depiction of a portion of the PFA coversheet supply web shown in FIG. 13A, following separation along separation perforations to form a PFA coversheet.

It will be appreciated that a sufficiently magnified plan view of separated side edges of PFA coversheets 17*a* will approximately reflect such dimensions and ratio. Referring to FIG. 13B, a PFA coversheet 17*a* processed according to the steps described herein (including such perforation step) will have a side edge oriented in the cross direction, having an appearance with features having similarities to those shown in FIG. 13B. There will be relatively neat edges 18*b* having cross direction dimensions approximately corresponding to length PL where the perforations were present (relatively easily identifiable and measurable with aid of suitable magnification equipment provided/combined with linear distance measuring aids), and tabs 18*c* where unperforated portions were present between the perforations, the distal ends of tabs 18*c* evidencing strain of the uncut portions of the film in the machine direction, to the point of failure of such portions of the film. The separation process imparts the tabs 18*c* with somewhat irregular lengths and irregularly-shaped distal end edges. Despite these irregularities, however, average lengths PSD and ratios average PL/(average PL+average PSD), or the two in combination, within the ranges set forth above, will result in relatively small and/or closely spaced tabs 18*c* that are not highly noticeable to the naked eye, retaining a neat appearance for the side edges of the PFA coversheet 17*a*. For purposes herein of determining average values for PL and PSD for a given product, 10 examples of PFA coversheets from 10 examples of the product in question are measured, each along a randomly-selected sample portion of the edge in question, 1.6 cm in length. Averages of the 10 measurements for each value are then calculated.

Following separation of the series of pads 10*c* into individual folded pads in separation unit 307, the individual folded pads may be conveyed to a packaging phasing unit 308, configured to receive the pads and reposition/space them apart along the machine direction by an average predetermined distance suitable for individual packaging described as follows. Suitably spaced, individual folded pads 10*a* then emerge from packaging phasing unit 308 in configuration (VI) as shown in FIG. 11A.

Figure 14A:
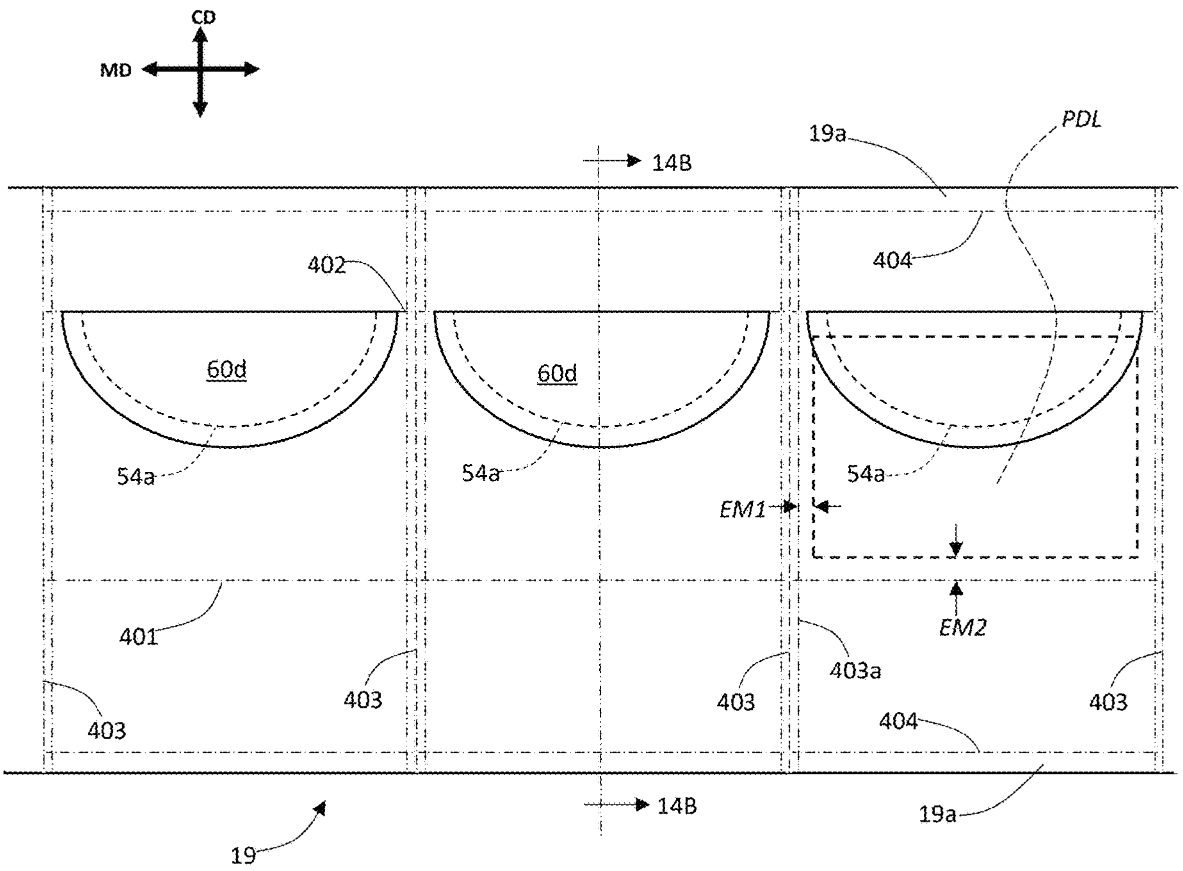
FIG. 14A is a plan view of a portion of continuous package film stock bearing applied flap stickers.
Figure 14B:
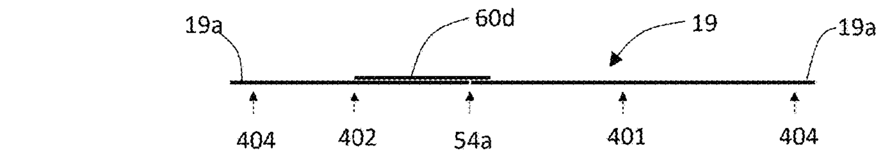
FIG. 14B is a cross section of the package film stock depicted in FIG. 14A, taken along line 14B-14B shown in FIG. 14A.

In configuration (VI), the individual folded, spaced pads 10*a* may be conveyed to a flow-wrap unit 311. Flow-wrap unit 311 may be configured to receive package film 19 from a package film supply roll 309. In some examples the package film may be predominately polyethylene, of an average caliper no greater than 0.08 mm (80 μm), preferably no greater than 0.065 mm (65 μm) and even more preferably no greater than 0.05 mm (50 μm). Referring to FIGS. 14A and 14B in conjunction with FIG. 11A, package film 19 already bearing pre-applied flap stickers 60*d* overlying preformed package opening cuts or perforations 54*a* in the film 19, may be received by flow-wrap unit 311. Alternatively, package film 19 may be received already bearing pre-applied flap stickers, but the film may yet to have package opening cuts or perforations 54*a* provided; and flow-wrap unit 311 may include or be preceded by a package film process unit 310 that provides package opening cuts or perforations 54*a* in package film 19. Alternatively, package film process unit 310 may be configured to perform either or both of application of flap stickers 60*d* to the package film 19, and provision of package opening cuts or perforations 54*a* in the package film 19.

Package opening cuts or perforations 54*a* may be intermittent perforations or continuous cuts that penetrate substantially or all of the entire thickness/caliper of the package film 19 along the intended path of separation. A supplier of pre-cut package film, or the manufacturer of the product who performs such perforating or cutting, may be provided advantage by application of flap stickers 60*d* to the film prior to perforating or cutting. Perforating or cutting may be performed continuously using roller-based die-cutting equipment, and the presence of stickers 60*d* makes it unnecessary to adjust the equipment such that the die cutting blade edges contact an opposing anvil roller to effect a cut through substantially the entire caliper or thickness of the film. Rather, previously-placed flap stickers 60*d* on the film 19 can effectively provide relatively soft “anvil” surfaces against which the die cutting blades operate. Clearances in the cutting equipment may be adjusted such that the die-cutting blades substantially penetrate/cut through the film 19, but not the flap stickers. In this manner, die cutting blade life may be extended because the die-cutting blade edges are not required to contact a relatively hard surface of an opposing anvil roller.

A continuous cut 54*a* in the film along the intended opening edge 54, in contrast to intermittent perforations, may provide a benefit for the consumer/user in that no tearing of package film 19 (at uncut or unperforated portions between perforations) is required to open the package, thereby generating less noise by opening the package.

Figure 15:
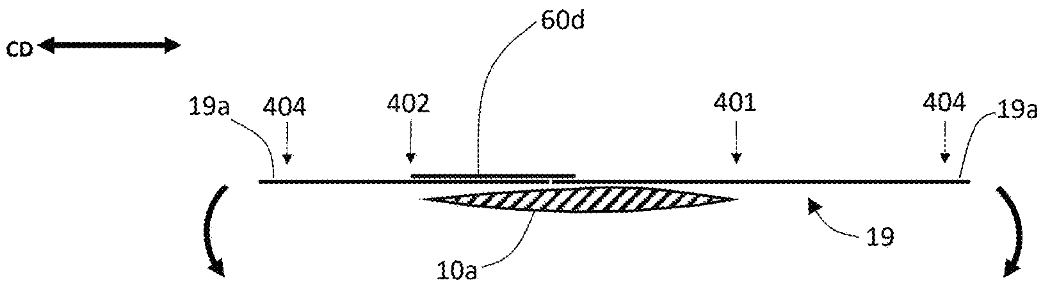
FIG. 15 is a view of the cross section of FIG. 14B, further depicting a location of disposition of a folded pad relative thereto, in preparation for flow wrapping.
Figure 16:
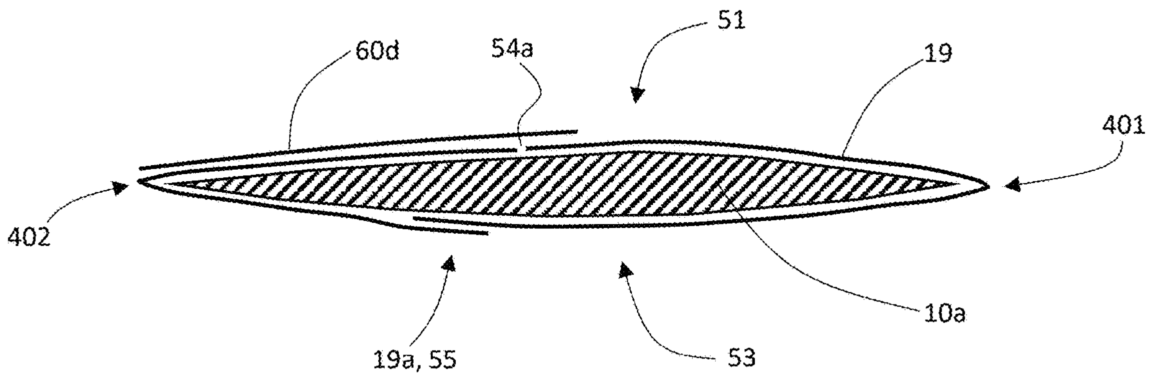
FIG. 16 is an expanded cross section view of the elements depicted in FIG. 15, following their exit from a flow-wrap unit.

As it continuously intakes package film 19, flow-wrap unit 311 also intakes the spaced (phased), individual folded pads 10*a* and successively disposes them in contact with the package film 19 along pre-determined (phased) intervals wherein the pad machine direction spacing corresponds and is registered with the film such that each pad is substantially evenly disposed/aligned between side crimp/seal/cut lines 403 along the cross direction CD of the film, and between package bottom and top fold lines 401 and 402. Such disposition is illustrated by way of example by pad disposition location PDL shown in FIG. 14A. Referring to FIGS. 15 and 16, flow-wrap unit 311 may be configured to then continuously wrap package film 19 over and about the succession of advancing pads 10*a* (e.g., via plow folding equipment). Referring again to FIG. 14A, package film 19 may be provided with seam margins 19*a* of extra film material extending (in the cross direction) outboard of seam margin lines 404, to provide material to create a continuous machine-direction seam 55 joining the machine-direction edges of the package film 19 after it is wrapped about the pads 10*a*. The flow-wrap unit 311 may include or be accompanied by equipment for forming the seams via use of adhesive, via thermal fusion of the package film, or a combination thereof, along the seam margins 19*a*. The seaming equipment may be configured to form a continuous machine-direction fin seam (such as shown in cross section, by way of example, in FIG. 10B (seam 55)), or alternatively, an overlap seam (such as shown in cross section, by way of example, in FIG. 16 (seam 55)). As previously noted in some examples it may be desired that attachment between the joined sections forming back panel 53, at seam 55, whether effected by adhesive or by welding/fusion of the film, be intermittent or discontinuous and may have spaced intervals of attachment, rather than being continuous, along seam 55. This may be desired to allow venting of air from within the finished package upon compression of the package, such as may occur in processes downstream of package formation, reducing chances that the package will burst open along seams or along the flap closure such as upon compression of the completed package.

A continuous series of flow-wrapped pads 10*d* emerge from the flow-wrap unit 311 in configuration (VII), also depicted by way of example, in cross section, in FIG. 16. In configuration (VII), the series 10*d* may be conveyed to a package crimp scaling and cutting unit 312. Package crimp sealing and cutting unit 312 may be configured to continuously receive the series 10*d* and then, at intervals corresponding to side crimp/seal/cut lines 403 (see FIG. 14A) crimp the package film 19 to form front and rear panels 51, 53 together, adhere or fuse the package film of the respective panels to form cross direction side seams 52 (illustrated in, e.g., FIGS. 5A and 9A) and cut the individual packages apart between successive trailing and leading portions of the seamed film material. Individual pad packages 10*e*, in configuration (VIII), emerge from the package crimp scaling and cutting unit 312, and may then be conveyed to a stacker (not shown) for controlled collection, orderly stacking and further packaging of quantities of individual packages, as desired. Adhesion or fusion of the package film of the front and rear panels to form side seams 52, and/or cutting between successive leading and trailing packages, may be effected by direct, localized application of heat, ultrasonic energy or any other mechanism suitable to effect localized joining of the film of the front and rear panels. In some examples, seaming and cutting may occur simultaneously, via, e.g., a heated, appropriately shaped knife or die.

Figure 11B:
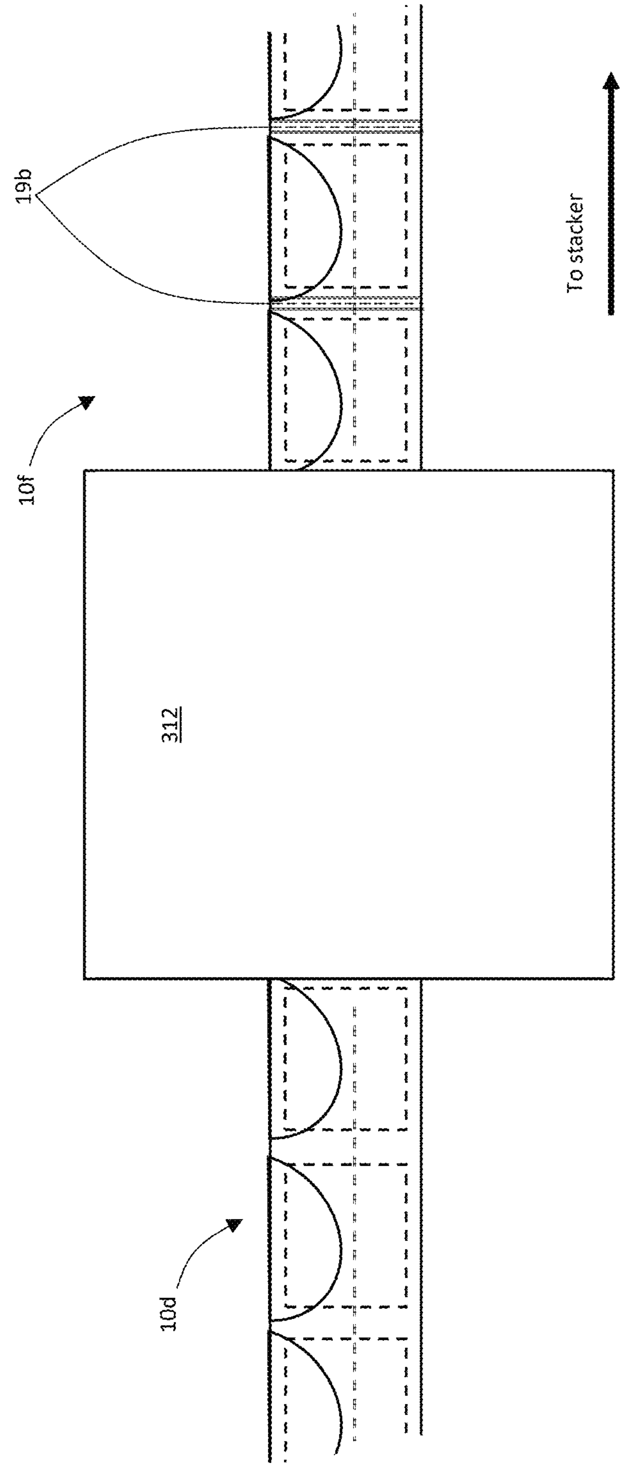
FIG. 11B is a schematic plan view depiction of an alternative example of a portion of the process flow depicted in FIG. 11A.

In some examples, rather than cutting the individual packages apart entirely as suggested in FIG. 11A, as suggested in FIG. 11B, unit 312 may be configured to create package separation perforations 19*b* between the formed seams of respective leading and trailing packages, as they pass through the unit, resulting in a continuous chain 10*f* of individual packages held together by the uncut portions of film within/along the paths of the package separation perforations 19*b* between the respective package side seams of adjacent leading and trailing packages. This provides a chain of packages 10*f* that may be gathered by rolling, or folding or festooning with each other in, e.g., accordion-fashion, in a desired quantity, for a desired alternative mode of packaging and/or dispensation. Packages supplied in this mode may be separated from each other by tearing along the package separation perforations 19*a*.

It is also contemplated that processes by which individual pads are flow-wrapped and envelope packages are formed thereabout, described above, may be applied in other examples wherein the folded pads are conveyed into flow wrapping unit 311 with their longitudinal axes oriented in the machine direction MD, rather than in the cross direction CD as described above. The resulting individually packaged pad will appear in the package with one side edge exposed at the access opening when the package is opening, and the other side edge within the package proximate the opposite, closed end of the package.

Packaging Process Adhesive

For purposes of minimizing the size of individual pad packages 10*c*, and making most efficient use of package film 19, it may be desired to size the design of the individual packages such that, following formation of the package about the folded pads 10, margins of space inside the packages, from locations about the respective outer edges of the folded pad 10*a* to the proximate folds or seams defining the space within the envelope packages, are minimized. Referring to FIGS. 11A and 14A, for example, assume pad disposition location PDL (shown in FIG. 14A) outlines the outer edges of the folded pad as it is located and placed into contact with the package film 19, upstream of flow wrap unit 311. It will be appreciated that margins EM1 and EM2 within the package envelope, between the outer edges of the folded pad and the respective proximate fold lines 401, 402 (EM2) and inner side crimp/seal lines 403*a* (EM1) delimiting the space inside the envelope, may be configured to be as small as feasibly possible, to minimize the sizes of the resulting pad packages 10*c* and maximize efficiency of use/consumption of packaging film stock 19. Minimizing margins EM1 and EM2, however, increases chances that edges of the folded pad as placed may accidentally stray beyond intended pad disposition location PDL relative the package film as the pad and film are conveyed through the processing line, and as a result be, undesirably, caught between crimping, scaling and/or cutting jaws or dies in, for example, package crimp seal and cut unit 312, or other package forming equipment, resulting in a defective and/or defectively-packaged product.

Figure 11C:
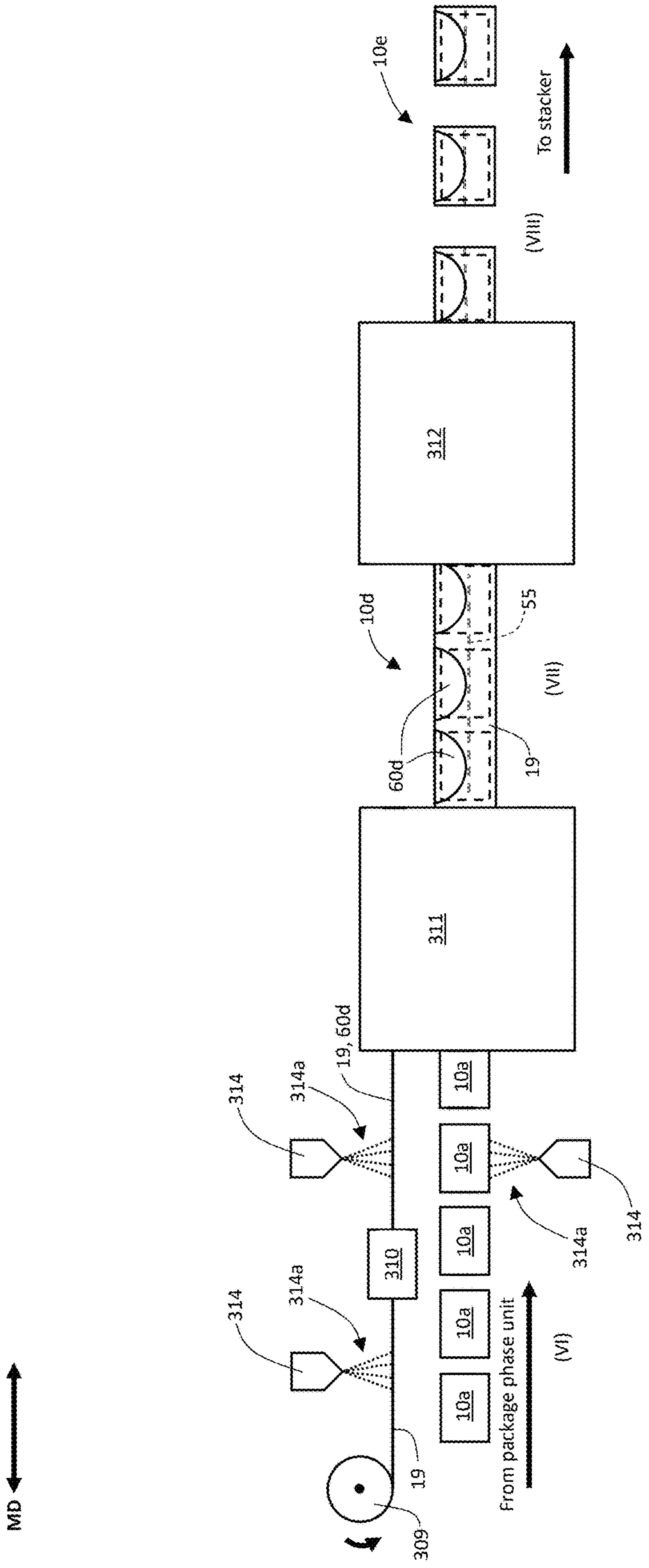
FIG. 11C is a schematic plan view depiction of an alternative example of a portion of the process flow depicted in FIG. 11A.

It has been learned that, to address and mitigate this problem, either or both of the folded pads 10*a* and the package film 19 may have a process adhesive applied thereto, to affix the folded pads 10*a* to the package film 19 prior to flow wrapping and/or prior to crimping, scaling and cutting away of pad package 10*e*. Referring to FIG. 11C, for example, process adhesive application units 314 may be disposed along the processing line in any suitable position or combination of positions that is/are upstream of the flow wrapping unit 311 and/or flow wrapping process, and disposed and configured to apply process adhesive 314*a* to surfaces of incoming folded pads 10*a*, to package film 19, or to both, in locations where the respective surfaces of each are to be disposed in facing contact with each other during flow wrapping and subsequent crimping/scaling/cutting away of individual pad packages 10*e*. As a result, upon placement of the outer surfaces of the folded pads 10*a* in facing contact with package film 19, the pads and film are adhered together, such that the pads are held in the desired position on and relative the film 19 during flow wrapping and during subsequent seaming and cutting, in package crimp seal and cut unit 312. This will reduce chances that pads 10*a* can be dislodged and/or mislocated from their intended positions in contact with package film 19, and thereby have portions undesirably caught between crimping, sealing and or cutting dies or other tooling in downstream processing equipment such as package crimp seal and cut unit 312.

The process adhesive 314*a* used may be any formulation suitable for adhering the respective materials forming the outer surfaces of folded pads 10*a*, and the package film, together, without causing breakdown or degradation of the respective materials that are adhered together. By way of non-limiting example, if the pads include features and are folded as described herein with PFA coversheets facing out, the PFA coversheets are made of polyethylene and the package film 19 is made of polyethylene, any process adhesive that bonds with polyethylene (without causing substantial breakdown or degradation of the polyethylene) may be deemed suitable. In other examples, the pad backsheets 30 may constitute the outer surfaces of the folded pads 10*a*, and these may be adhered to the package film 19 as described above. Generally it will be desired that the process adhesive formulation, when applied, does not cause substantial breakdown or degradation of materials constituting outer surfaces of the folded pad 10*a* and inner surfaces of the package film 19. In some examples the adhesive may be a hot melt adhesive.

Noting that adhering the folded pad 10*a* to the package film 19 may increase effort required of the consumer/user of the pad to remove it from the pad package 10*e*, it may be desired to take steps to mitigate or eliminate this effect.

For purposes of both case of separation, consumer quality perception, retention of pad structural integrity and functionality, and retention of envelope package utility as a disposal aid (following pad use), it is desirable that at least the materials of the pad, and also preferably materials and seams of the package envelope 50, not be torn, perforated, plastically deformed or otherwise substantially damaged upon removal of the pad 10*a* from the package envelope 50. In some examples, the process adhesive formulation may be selected so as to be non-destructively removable, e.g., permit relatively easy peeling away, of the respective facing surfaces from teach other, without tearing or permanent/plastic deformation of either or both of package film 19/package envelope 50, and the material(s) constituting the outer surface(s) of the folded pad 10*a*.

Additionally or alternatively, it may be desired that the quantity (e.g., basis weight) and surface area coverage of the process adhesive 314*a*, as applied, be minimized, to provide only enough holding strength and resistance to displacement (which may be needed mainly along shearing directions), to accomplish the purpose described above, while still requiring only minimal effort by the consumer/user to peel the folded pad 10*a* away from the inner surfaces of the package 50/10*e*. Thus, for example, the process adhesive 314*a* may be applied in any suitable discontinuous pattern, such as a pattern of solid or dashed line segments, stripes, spirals, dots, etc. In other examples, a random pattern of discrete spots and/or areas of a thin film of adhesive may be created, resulting from deposition of individual sprayed droplets of process adhesive, and subsequent compression thereof between the pad and the package film.

The adhesive may be applied to a basis weight at a level selected to maximize efficient usage of process adhesive 314*a* material, while providing the desired level of effective holding force. Accordingly, for purposes described herein, the adhesive may be applied to a basis weight of 2 gsm to 8 gsm, more preferably 3 gsm to 7 gsm, and even more preferably 4 gsm to 6 gsm.

In some examples, the process adhesive selected may be formulated to have only temporary adhesive properties, such that it loses adhesion over time-such that it holds the folded pad 10*a* and package film 19 together as needed during packaging, but then, following packaging, loses adhesive properties and/or bonding strength by the time the product reaches consumers'/users' hands, such that the pad may be removed from the package by the consumer/user without substantial resistance caused by the process adhesive. Formulations are contemplated in which one or more components of the process adhesive evaporate, causing the process adhesive to lose its tackiness or bond strength. Other formulations are contemplated in which components of the process adhesive formulation react with each other and/or with ambient air over time, to cause a chemical change that effects loss of adhesion or bond strength. In some examples, the process adhesive selected may be, or include, a frangible bonding agent, examples of which are disclosed in U.S. Pat. No. 9,610,202. Such agents may be formulated and selected for exhibiting a bond strength that decays over time, or additionally or alternatively, exhibiting a transition over time following application, to a brittle composition that is relatively easy to fracture. In some examples, the adhesive may be a hot-melt adhesive that can be applied via a spray apparatus when in molten/liquid form.

In some examples, the PFA coversheet stock 17 (or other material constituting the outer surface of the folded pad 10*a*) may be formed of a first polymer composition, and the package film 19 may be formed of second, differing polymer composition. The process adhesive 314*a* selected may be formulated so as to more readily and/or aggressively remain adherent to one or to the other of the compositions of the package film 19 material and the PFA coversheet stock 17 (or other pad outer surface), so that when the consumer/user removes the folded pad 10*a* from the envelope package 50, the process adhesive material tends to remain adhered to either the inside of the package, or the PFA coversheet 17*a* (or other outer surface of the folded pad 10*a*), as desired. This is to reduce chances that process adhesive material will separate and peel or flake away from both surfaces when the consumer/user removes the pad from the envelope package 50, which could have a negative effect on the consumer/user's perception of product quality. For purposes of consumer perception, it may be desired that the combination of components of package film 19, components of PFA coversheet stock 17 (or other material forming the outer surface of folded pad 10*a*), and process adhesive 314*a* formulation, be selected such that the process adhesive 314*a* tends to adhere more aggressively to the inside surface of package film 19/envelope package 50, and conversely, tends to release more easily from the PFA coversheet 17*a* of the pad 10*a*, such that the process adhesive tends to remain with the package envelope 50 when the consumer/user removes the pad 10*a* therefrom. This relationship can be identified by peeling the pad 10*a* from the package film 19, and determining which of the two surfaces the process adhesive tends to remain adhered to, following separation.

Additionally, or alternatively, it may be desired that the package film 19 and the PFA coversheet stock 17 are manufactured to have differing basis weights. Generally, for respective sheet/web materials having similar compositions as contemplated herein, the material having the greater basis weight will have the greater bending stiffness, and the material having the lesser basis weight will have the lesser bending stiffness. Thus, when a consumer user peels the adhered materials away from each other, the material with the lesser basis weight and lesser bending stiffness will more readily separate from a process adhesive disposed between the two materials, because it will more readily flex and bend away from the interface, making it more susceptible to peeling. Thus, for purposes of consumer perception as noted above, it may be desired that PFA coversheet stock 17 have a lesser basis weight than package film 19.

Additionally, or alternatively, in some examples, the process adhesive 314*a* may be a hot melt adhesive selected and/or formulated so as to have a polymer composition that is miscible in the melted phase with the polymer composition of the film to which it is first applied ("first film"), in the process. (The "first film" to which hot melt process adhesive 314*a* is applied may, in some examples, be package film 19.) The hot melt adhesive 314*a* is heated to its melt phase for application. The application temperature of the adhesive 314*a* may be controlled such that it is equal to or greater than the melt temperature of the first film, or surface layer or portion thereof, to which it is applied. When the hot melted process adhesive 314*a* first contacts the first film, some melting and blending of the respective polymer(s) of the process adhesive and the polymer(s) of the first film may occur at or proximate the interface therebetween, resulting in some fusing between the process adhesive material and the first film material, upon cooling. This may cause the process adhesive material to be relatively more aggressively bonded to the first film, than to the film to which it is next applied ("second film"). (The "second film" which contacts the process adhesive following its application to the first film may, in some examples, be film forming the outer surfaces of the folded pad (e.g., backsheet adhesive coversheet stock 17).) Because the first film and the second film are brought together subsequent to initial application of the process adhesive 314*a* to the first film, the process adhesive has time to cool somewhat, from its initial application temperature, before contact with the second film, such that less or no fusion bonding will occur between the process adhesive and the second film. As a result, the process adhesive material may be more strongly bonded to the first film than to the second film. In these circumstances, the bond between the process adhesive 314*a* material and the first film may be a combination of fusion bonding and adhesive bonding, and the bond between the process adhesive 314*a* material and the second film may be more likely, predominantly, adhesive bonding.

In some examples, the second film (e.g., backsheet adhesive coversheet stock 17) may have additional features that reduce adhesion thereto, by the applied process adhesive 314*a*. In some examples, the second film may be embossed or micro-embossed to impart a persistent pattern of relatively small z-direction deformations, having, for example, relatively small peaks or ridges and depressions or valleys, in an alternating pattern. This feature can cause bonding between the second film and the process adhesive to be intermittent, such that, for example, upon contact with the second film the process adhesive contacts surfaces of only the peaks or ridges, and not surfaces of the depressions or valleys. As a result, bonding between the process adhesive and the second film may be caused to be comparatively less aggressive, than bonding between the process adhesive and the first film.

Additionally or alternatively, in some examples, the second film may have a surface layer of a varnish or other material that differs from the polymer composition of the surface of the first film, wherein the process adhesive bonds less aggressively to the varnish or other material, than to the surface(s) of the first film. In some examples, the second film may bear deposit(s) of ink disposed to impart color or decorative artwork to the second film, wherein the ink serves a secondary purpose of causing the process adhesive 314*a* to bond less aggressively to the surface(s) of the second film, than to the surface(s) of the first film.

Figure 11D:
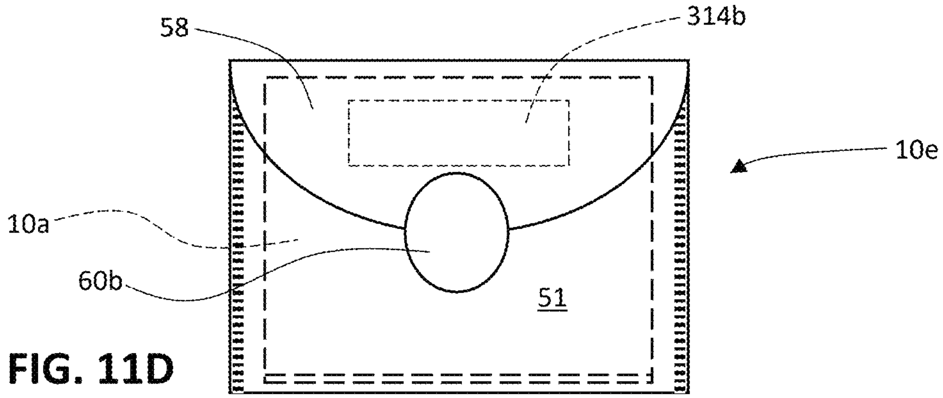
FIGS. 11D and 11E are depictions of an example of a pad package in closed (FIG. 11D) and opened (FIG. 11E) configurations.
Figure 11E:
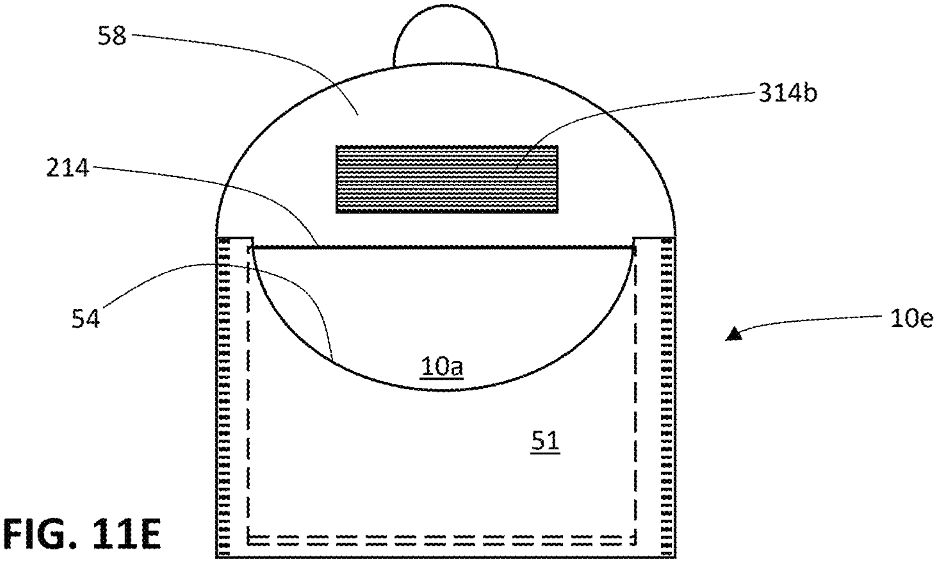

In some examples, a weight majority or substantially all of the process adhesive 314*a* that is applied, may be applied to a portion of the package film 19 defined or limited to one that is to serve as a removable, liftable and/or other opening portion of the finished package envelope 50. For example, referring to FIGS. 5A, 5B, 8, 9A, 9B, 10C, and 11C-11E, the process adhesive application units 314 and the processing line may be configured such that process adhesive 314*a* is applied to an inward-facing surface of the package film 19, substantially only on a portion of the package film 19 that is to constitute liftable opening flap 58 of the finished package envelope 50. If the finished package envelope 50 and pad package 10*c* has been processed and configured in this manner, when the user/consumer lifts the opening flap 58 to open the pad package 10*c*, they simultaneously separate the opening flap from the pad 10*a* therewithin, and thereby break the adhesion between the pad and the package envelope 50, facilitating removal of the pad 10*a* from the package envelope 50. Referring to FIGS. 11D and 11E, for example, a deposit 314*b* of process adhesive may be applied to the inside surface of a closure flap 58. When the consumer/user opens the package by lifting closure flap 58, they can, simultaneously with opening of the package, separate the process adhesive deposit 314*b* from the folded pad 10*a*. When the pad package is manufactured in this configuration, it will be appreciated that disposing a singularized fold nose 214 (shown in FIGS. 4A-4C and 11E) of the folded pad 10*a* proximate the opening, as described above, may be advantageous, because it increases the case and simplicity for the consumer, grasping the bottom of the pad package 10*c* (and indirectly, the folded pad 10*a* therein) in one hand and the edge of the opening flap 58 in the other, to simultaneously lift the opening flap 58 and peel the package film of the flap 58 thereof away from the folded pad 10*a*. For similar reasons, it may be desired that the folded pad 10*a* be folded in a book jacket fold configuration as illustrated in FIG. 4B, and described above. This avoids a situation in which a free forward or rearward end of the pad is adhered to the opening flap, which can complicate the flap opening and package/pad separation step, for the consumer/user.

It will be appreciated that any combination of the steps and features described above, relating to process adhesive, may be desired, to provide for suitable effective holding strength between the pad 10*a* and the package film 19 during packaging. Additionally, any combination of the steps and features described above may be desired, to provide for relative ease for the consumer/user, of removal of the pad 10*a* from the package envelope 50/pad package 10*e* for use.

One or more process adhesive application units 314 may have any configuration suitable for applying the process adhesive 314*a* formulation selected. In some examples, a process adhesive application unit 314 may be a spray apparatus configured to spray a process adhesive formulation in molten or other flowable/liquid form. The spray apparatus may include a spray nozzle and may be configured with a controllable valve system that effects starting and stopping of adhesive flow and/or spray, to enable intermittent, package-by-package application of process adhesive to designated areas of package film 19. In other examples, the process adhesive application unit 314 may be a roll or kiss coater, a gravure roller or similar device configured to use a roller to transfer process adhesive in liquid form from a reservoir to a surface of package film 19. The roller may be patterned and suitably configured so as to effect selectively placed, rather than continuous, application of adhesive. In other examples, an extruder or a slot coater may be used. In examples in which the package film bears pre-cut perforations or other cut material edges extending along a cross direction at the time the process adhesive is applied, however, it may be preferred that the process adhesive application unit be a spray apparatus or a roller apparatus, because the cut edges could, undesirably, catch on features of an extruder or slot coater.

For purposes of consumer perception (e.g., to avoid causing a perception of contamination, or excess or misplaced adhesive), it may be desired that the process adhesive 314*a* as applied and as remaining in place on a surface following separation of the pad 10*a* from the envelope package 50, not be substantially visually noticeable to the consumer/user, upon opening of the pad package 10*e* and removal of the folded pad 10*a* therefrom. Accordingly, it may be desired that the adhesive formulation be substantially colorless and translucent or even transparent as applied, or alternatively, has a color that substantially matches the color of the underlying material to which it is adhered, following peeling away and separation of the pad 10*a* from the package envelope 50. Thus, it may be desired that the applied process adhesive, and the material forming the outer surface(s) of the pad 10*a* and/or the inner surface(s) of the package envelope to which the pad 10*a* is adhered prior to separation, not exhibit a visual contrast (as defined above) between the portions of a surface bearing process adhesive and the adjacent portions of surface not bearing process adhesive.

Visual Contrast Method

The color difference measurement is based on the CIE L*a*b* color system (CIELAB). A flatbed scanner capable of scanning a minimum of 24 bit color at 1200 dpi and has manual control of color management (a suitable scanner is an Epson Perfection V750 Pro from Epson America Inc., Long Beach CA) is used to acquire images. The scanner is calibrated against a color reflection target compliant to ANSI method IT8.7/2-1993 using color management software (a suitable package is MonacoEZColor available from X-Rite Grand Rapids, MI) to construct a scanner profile. The resulting calibrated scanner profile is opened within an imaging program that supports sampling in CIE L*a*b* (a suitable program is Photoshop S4 available from Adobe Systems Inc., San Jose, CA) to measure bonded and unbonded areas.

Turn on the scanner for 30 minutes prior to calibration. Place the IT8 target face down onto the scanner glass and close the scanner lid. Open the MonacoEZColor software and select acquire image using the Twain software included with the scanner. Within the Twain software deselect the unsharp mask setting and any automatic color correction or color management options that may be included in the software. If the automatic color management cannot be disabled, the scanner is not appropriate for this application. Acquire a preview scan at 200 dpi and 24 bit color. Insure that the scanned image is straight and first outer surface facing side-up. Crop the image to the edge of the target, excluding all white space around the target, and acquire the final image. The MonacoEZColor software uses this image to compare with included reference files to create and export a calibrated color profile compatible with Photoshop. After the profile is created the scan resolution (dpi) can be changed, but all other settings must be kept constant while imaging samples.

Provide respective samples of each portion of material to be compared 75 mm by 75 mm square. Precondition the samples at about 23° C.±2 C.° and about 50%±2% relative humidity for 2 hours prior to testing.

Open the scanner lid and place the first sample onto the scanner glass with the first outer surface facing the glass. Cover the sample with the white background (in this test method white is defined as having L*>94, −2<a*<2, and −2<b*<2) and close the lid. Acquire and import a scan of the first sample into Photoshop at 600 dpi and 24 bit color. Assign the calibrated scanner profile to the image and change the mode to Lab Color ("Lab Color" in Photoshop corresponds to the CIE L* a* b* standard). Select the "eyedropper" color selection tool. Set the sampling size of the tool to include as many pixels as possible within an area of the sample 2 mm by 2 mm square. Using the eyedropper tool measure and record L*a*b* values in 10 different 2 mm by 2 mm square areas (not having apertures) in the sample image. Average the 10 individual L*a*b* values and record as L1, a1, and b1, respectively.

Repeat the steps in the paragraph above for the second sample, and record the averaged values as L2, a2 and b2. Calculate and report the color difference (delta E*) between the bonded and unbonded areas using the following equation:

$$\text{delta } E^* = \sqrt{(L_2^* - L_1^*)^2 + (a_2^* - a_1^*)^2 + (b_2^* - b_1^*)^2}$$

and report to the nearest 0.01 units. A total of three substantially identical samples of each layer are measured for each sample set. Average the three delta E* values and report to the nearest 0.1 unit.

In view of the foregoing description, the following non-limiting examples are contemplated:

1. A process for producing individual feminine hygiene pad packages (10*e*), comprising the steps of:
   - providing a continuous series of successive folded individual feminine hygiene pads (10*b*) moving along a machine direction, each of the pads comprising a topsheet (20), a backsheet (30), and an absorbent structure (40) disposed between the topsheet and the backsheet;
   - providing a continuous supply of package film (19) having an inward surface and an outward surface and moving along the machine direction,
   - applying a process adhesive (314*a*) to one or both of the folded pads (10*a*) and the inward surface of the package film (19);
   - disposing the folded pads (10*a*) in facing contact with the inward surface of the package film (19) and thereby adhering the folded pads to the package film;
   - conveying the package film (19) and the adhered pads (10*a*) together to flow wrapping equipment (311), and thereby wrapping the package film (19) about the pads (10*a*) and creating a continuous series of flow-wrapped pads (10*d*);
   - conveying the series of flow-wrapped pads (10*d*) to package seaming equipment (312), to form package seams (52) along the series of flow-wrapped pads, between successive leading and trailing pads, thereby forming a series of individually enveloping package structures about respective individual pads; and
   - conveying the series of individually enveloping package structures to package cutting, separating and/or perforating equipment (312), to form separate or separable individual pad packages (10*e*) each comprising an envelope package (50) containing a folded pad (10*a*).
2. The process of example 1 wherein the process adhesive (314*a*) has a formulation that loses strength and/or adhesive properties with passage of time, subsequent to formation of the pad packages (10*e*).
3. The process of either of the preceding examples wherein the process adhesive (314*a*) is applied via spraying apparatus or roller.
4. The process of any of the preceding examples wherein the feminine hygiene pads (10*b*) each comprise a deposit of panty-fastening adhesive (35) applied to an outward-facing surface of the pad, and a PFA coversheet (17*a*) covering the panty-fastening adhesive, and the PFA coversheet forms outer surfaces of the pads as folded.

5. The process of example 4 wherein the PFA coversheet (17*a*) and the package film (19) have differing compositions.
6. The process of example 5 wherein the process adhesive (314*a*) exhibits greater adhesion to one of the PFA coversheet (17*a*) and the package film (19), than to the other.
7. The process of example 6 wherein the process adhesive (314*a*) exhibits greater adhesion to the package film (19), than to the PFA coversheet (17*a*).
8. The process of any of examples 4-7 wherein the PFA coversheet (17*a*) and the package film (19) each comprise a polyolefin.
9. The process of any of examples 4-8 wherein the PFA coversheet (17*a*) has a first basis weight, and the package film (19) has a second basis weight, and the first basis weight differs from the second basis weight, and preferably, the first basis weight is less than the second basis weight.
10. The process of any of examples 4-9 wherein the process adhesive (314*a*) is a hot melt adhesive.
11. The process of any of examples 4-10 wherein the process adhesive, and at least one of the package film (19) and PFA coversheet (17*a*), have fusion bonds formed therebetween.
12. The process of any of examples 4-11 wherein at least one of the package film (19) and PFA coversheet (17*a*) is imparted with a pattern of embossing or microembossing.
13. The process of any of examples 4-12 wherein at least one of the package film (19) and PFA coversheet (17*a*) bears a coating of varnish or other material differing in composition from a surface of the other of the package film and PFA coversheet.
14. The process of any preceding examples wherein the envelope packages (50) comprise opening flaps (58), and for each pad package (10*e*) a weight majority of the process adhesive (314*a*) is disposed between the pad (10*a*) and an inward-facing surface of the opening flap (58).
15. A feminine hygiene pad package (10*e*), comprising:
    a folded, individual feminine hygiene pad (10*a*), comprising a topsheet (20), a backsheet (30), and an absorbent structure (40) disposed between the topsheet and the backsheet, the pad (10*a*) being disposed within a flow-wrap envelope package (50); and
    a deposit of process adhesive (314*a*) disposed between the folded pad (10*a*) and material (19) constituting the envelope package (50).
16. The feminine hygiene pad package of example 15, wherein the deposit of process adhesive (314*a*) loses adhesive strength and/or adhesive properties with passage of time.
17. The feminine hygiene pad package of either of examples 15 or 16 wherein the deposit of process adhesive is disposed in a discontinuous pattern.
18. The feminine hygiene pad package of any of examples 15-17, wherein the feminine hygiene pad (10*a*) comprises a deposit of panty-fastening adhesive (35) applied to an outward-facing surface of the pad, and a PFA coversheet (17*a*) covering the panty-fastening adhesive.
19. The feminine hygiene pad package of example 18 wherein the PFA coversheet (17*a*) and material (19) constituting the envelope package (50) directly face each other, and the deposit of process adhesive (314*a*) is disposed between them.
20. The feminine hygiene pad package of either of examples 18 or 19 wherein material (19) constituting the envelope package (50) is film material comprising one or more polymers, and material constituting the PFA coversheet (17*a*) is film material comprising one or more polymers.
21. The feminine hygiene pad package of any of examples 18-20 wherein the material (19) constituting the envelope package (50) and material constituting the PFA coversheet (17*a*) have differing compositions.
22. The feminine hygiene pad package of any of examples 18-21 wherein the material (19) constituting the envelope package (50) and material (17) constituting the PFA coversheet (17*a*) have differing basis weights.
23. The feminine hygiene pad package of any of examples 15-22 wherein the process adhesive (314*a*) exhibits greater adhesion to one or the other of the material (19) constituting the envelope package (50) and material (17) constituting outer surfaces of the pad (10*a*) as folded.
24 The feminine hygiene pad package of any of examples 18-23 wherein the process adhesive (314*a*) is a hot melt adhesive.
25. The feminine hygiene pad package of any of examples 18-24 wherein the process adhesive (314*a*), and at least one of the package film (19) and PFA coversheet (17*a*), have fusion bonds formed therebetween.
26. The feminine hygiene pad package of any of examples 18-25 wherein at least one of the package film (19) and PFA coversheet (17*a*) is imparted with a pattern of embossing or microembossing.
27. The feminine hygiene pad package of any of examples 18-26 wherein at least one of the package film (19) and PFA coversheet (17*a*) bears a coating of varnish or other material differing in composition from a surface of the other of the package film and PFA coversheet.
28. The feminine hygiene pad package of any of examples 15-27 wherein the envelope package (50) comprises an opening flap (58), and a weight majority of the process adhesive (314*a*) is disposed between the feminine hygiene pad (10*a*) and an inward-facing surface of the opening flap (58).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for producing individual feminine hygiene pad packages, comprising the steps of:

providing a continuous series of successive folded individual feminine hygiene pads moving along a machine direction, each of the feminine hygiene pad comprising a topsheet, a backsheet, and an absorbent structure disposed between the topsheet and the backsheet;

providing a continuous supply of package film having an inward surface and an outward surface and moving along the machine direction;

applying a process adhesive to one or both of the folded pads and the inward surface of the package film;

disposing the folded pads in facing contact with the inward surface of the package film and thereby adhering the folded pads to the package film;

conveying the package film and the adhered pads together to flow wrapping equipment, and thereby wrapping the package film about the folded pads and creating a continuous series of flow-wrapped pads;

conveying the series of flow-wrapped pads to package seaming equipment, to form package seams along the series of flow-wrapped pads, between successive leading pads and trailing pads, thereby forming a series of individually enveloping package structures about respective individual pads; and conveying the series of individually enveloping package structures to package cutting, separating and/or perforating equipment, to form separate or separable individual pad packages each comprising an envelope package containing a folded pad, wherein the feminine hygiene pads each comprise a deposit of panty-fastening adhesive applied to an outward-facing surface of the pad, and a panty-fastening adhesive (PFA) coversheet covering the panty-fastening adhesive, and the PFA coversheet forms outer surfaces of the pads as folded, and wherein the process adhesive exhibits greater adhesion to one of the PFA coversheet and the package film, than to the other.

2. The process of claim 1 wherein the process adhesive is applied via a spraying apparatus or a roller.

3. The process of claim 1 wherein the PFA coversheet and the package film have differing compositions.

4. The process of claim 1 wherein the process adhesive exhibits greater adhesion to the package film, than to the PFA coversheet.

5. The process of claim 1 wherein the PFA coversheet and the package film each comprise a polyolefin.

6. The process of claim 1 wherein the PFA coversheet has a first basis weight, and the package film has a second basis weight, and the first basis weight differs from the second basis weight.

7. The process of claim 1 wherein the process adhesive is a hot melt adhesive.

8. The process of claim 1 wherein the process adhesive, and at least one of the package film and PFA coversheet, have fusion bonds formed therebetween.

9. The process of claim 1 wherein at least one of the package film and PFA coversheet is imparted with a pattern of embossing or microembossing.

10. The process of claim 1 wherein at least one of the package film and PFA coversheet bears a coating of varnish or other material differing in composition from a surface of the other of the package film and PFA coversheet.

11. The process of claim 1 wherein the envelope packages comprise opening flaps, and for each pad package a weight majority of the process adhesive is disposed between the pad and an inward-facing surface of the opening flap.

12. A process for producing individual feminine hygiene pad packages, comprising the steps of:

providing a continuous series of successive folded individual feminine hygiene pads moving along a machine direction, each of the feminine hygiene pad comprising a topsheet, a backsheet, and an absorbent structure disposed between the topsheet and the backsheet;

providing a continuous supply of package film having an inward surface and an outward surface and moving along the machine direction;

applying a process adhesive to one or both of the folded pads and the inward surface of the package film;

disposing the folded pads in facing contact with the inward surface of the package film and thereby adhering the folded pads to the package film;

conveying the package film and the adhered pads together to flow wrapping equipment, and thereby wrapping the package film about the folded pads and creating a continuous series of flow-wrapped pads;

conveying the series of flow-wrapped pads to package seaming equipment, to form package seams along the series of flow-wrapped pads, between successive leading pads and trailing pads, thereby forming a series of individually enveloping package structures about respective individual pads; and conveying the series of individually enveloping package structures to package cutting, separating and/or perforating equipment, to form separate or separable individual pad packages each comprising an envelope package containing a folded pad, wherein the feminine hygiene pads each comprise a deposit of panty-fastening adhesive applied to an outward-facing surface of the pad, and a panty-fastening adhesive (PFA) coversheet covering the panty-fastening adhesive, and the PFA coversheet forms outer surfaces of the pads as folded, wherein the PFA coversheet and the package film have differing compositions, and wherein the process adhesive exhibits greater adhesion to one of the PFA coversheet and the package film, than to the other.

13. The process of claim 12 wherein the PFA coversheet and the package film each comprise a polyolefin.

14. The process of claim 12 wherein the process adhesive is a hot melt adhesive.

15. A process for producing individual feminine hygiene pad packages, comprising the steps of:

providing a continuous series of successive folded individual feminine hygiene pads moving along a machine direction, each of the feminine hygiene pad comprising a topsheet, a backsheet, and an absorbent structure disposed between the topsheet and the backsheet;

providing a continuous supply of package film having an inward surface and an outward surface and moving along the machine direction;

applying a process adhesive to one or both of the folded pads and the inward surface of the package film;

disposing the folded pads in facing contact with the inward surface of the package film and thereby adhering the folded pads to the package film;

conveying the package film and the adhered pads together to flow wrapping equipment, and thereby wrapping the package film about the folded pads and creating a continuous series of flow-wrapped pads;

conveying the series of flow-wrapped pads to package seaming equipment, to form package seams along the series of flow-wrapped pads, between successive leading pads and trailing pads, thereby forming a series of individually enveloping package structures about respective individual pads; and conveying the series of individually enveloping package structures to package cutting, separating and/or perforating equipment, to form separate or separable individual pad packages each comprising an envelope package containing a folded pad, wherein the feminine hygiene pads each comprise a deposit of panty-fastening adhesive applied to an outward-facing surface of the pad, and a panty-fastening adhesive PFA) coversheet covering the panty-fastening adhesive, and the PFA coversheet forms outer surfaces of the pads as folded, and wherein the PFA coversheet has a first basis weight, and the package film has a second basis weight, and the first basis weight differs from the second basis weight.

16. The process of claim 15 wherein the process adhesive, and at least one of the package film and PFA coversheet, have fusion bonds formed therebetween.

17. The process of claim 15 wherein at least one of the package film and PFA coversheet is imparted with a pattern of embossing or microembossing.

* * * * *